United States Patent [19]
Laibovitz et al.

[11] Patent Number: 5,997,518
[45] Date of Patent: Dec. 7, 1999

[54] APPARATUS AND METHOD FOR DELIVERY OF SMALL VOLUMES OF LIQUID

[76] Inventors: Robert A. Laibovitz, 7506 Valley Dale Dr.; Robert L. Rogers, 7604 Long Point Dr., both of Austin, Tex. 78731

[21] Appl. No.: 09/006,720

[22] Filed: Jan. 14, 1998

[51] Int. Cl.⁶ .................................................. A61M 35/00
[52] U.S. Cl. .......................................... 604/296; 604/298
[58] Field of Search ..................................... 604/289, 290, 604/294, 296, 298; 222/333, 340, 360, 390, 387, 494

[56] References Cited

U.S. PATENT DOCUMENTS

| | | | |
|---|---|---|---|
| 3,934,585 | 1/1976 | Maurice | 128/225 |
| 4,623,337 | 11/1986 | Maurice | 604/298 |
| 5,053,000 | 10/1991 | Booth et al. | 604/289 |
| 5,207,659 | 5/1993 | Pennaneac'h et al. | 604/298 |
| 5,630,793 | 5/1997 | Rowe | 604/289 |
| 5,685,869 | 11/1997 | Py | 604/294 |

OTHER PUBLICATIONS

Bartlett and Jaanus, "Drugs affecting the autonomic nervous system," In: *Clinical Ocular Pharmacology*, 2nd ed., Butterworths, Boston, pp. 95–148, 1989.

Brown et al., "Creating smaller eyedrops by reducing eyedropper tip dimensions," *Am. J. Ophthalmol.*, 99:460–464, 1985.

Brown et al., "Improving the therapeutic index of topical phenylephrine by reducing drop volume," *Ophthalmol.*, 94(7):847–850, 1987.

Brown et al., "Reducing eyedrop size decreases systemic asorption of 10% phenylephrine," *ARVO Abstracts*, 27(3):102, 1986.

Chader et al., In: *Pharmacology of the Eye, Handbook of Experimental Pharmacology*, vol. 69, Sears ed., Springer–Verlag, Berlin, 1984.

Chattoraj and Birdie, "Experimental methods and procedures," In: *Adsorption and the Gibbs Surface Excess*, Plenum Press, New York, pp. 21–38, 1984.

Chattoraj and Birdie, "Wettability and contact angles," In: *Adsorption and the Gibbs Surface Excess*, Plenum Press, New York, pp. 233–256, 1984.

Chrai et al., "Drop size and initial dosing frequency problems of topically applied ophthalmic drugs," *J. Pharm. Sci.*, 63(3):333–338, 1974.

Chrai et al., "Lacrimal and instilled fluid dynamics in rabbit eyes," *J. Pharm. Sci.*, 62(7):1112–1121, 1973.

File and Patton, "Topically applied pilocarpine: human pupillary response as a function of drop size," *Arch. Aphthalmol.*, 98:112–115, 1980.

Fox and McDonald, "Basic equations in integral form for a control volume," In: *Introduction to Fluid Mechanics*, 4th ed., Wiley & Sons, New York, pp. 96–129, 1992.

Gosline and Morrough, "The water jet pump," In: *Univ. Calif. Publ. Engin.*, Univ. Calif. Press, 3(3):167–190, 1934.

Gray, "The influence of drop size on pupil dilation," *Eye*, 5:615–619, 1991.

Harkins and Brown, "The determination of surface tension (free surface energy), and the weight of falling drops: the surface tension of water and benzene by the capillary height method," *J. Am. Chem. Soc.*, 41:499–524, 1919.

Himmelstein et al., "Preliminary pharmacokinetic model of pilocarpine uptake and distribution in the eye," 67(5):603–606, 1978.

Jumpeter, "Jet pumps," In: *Pump Handbook*, 2nd Ed., McGraw Hill, Chapter 4, pp. 4.1–4.27 1986.

Landau and Lifshitz, "Surface phenomena," In: *Fluid Mechanics*, 2nd ed., Butterworth and Heinemann, eds., Linacre House, 6:238–250, 1987.

(List continued on next page.)

*Primary Examiner*—Ronald Stright
*Assistant Examiner*—David J. Cho

[57] ABSTRACT

Device and method for delivering small microliter volumes of liquid preparations to the eye or other body part utilizing a gas stream to induce a controlled, preselected volume of liquid into the gas stream and to deliver the liquid in the form of small droplets to the desired site.

10 Claims, 7 Drawing Sheets

OTHER PUBLICATIONS

Lynch et al., "Reduction of phenylephrine drop size in infants achieves equal dilation with decreased systemic absorption," *Arch. Ophthalmol.,* 105:1364–1365, 1987.

Patton and Francoeur, "Ocular bioavailability and systemic loss of topically applied ophthalmic drugs," *Am. J. Ophthalmol.,* 85:225–229, 1978.

Patton, "Pharmacokinetic evidence for improved ophthalmic drug delivery by reduction of instilled volume," 66(7):1058–1059, 1977.

Petursson et al., "Treatment of glaucoma using minidrops of clonidine," *Arch. Ophthalmol.,* 102:1180–1181, 1984.

Schoenwald, "Pharmacokinetics in ocular drug delivery," In: *Biopharmaceutics of Ocular Drug Delivery,* CRC Press, Inc., City, pp. 159–191, 1993.

Shell, "Pharmacokinetics of topically applied ophthalmic drugs," *Survey Ophthalmol.,* 26(4):207–218, 1982.

Vocci et al., "Reformation and drop size of apraclonidine hydrochloride," *Am. J. Ophthalmol.,* 113:154–160, 1992.

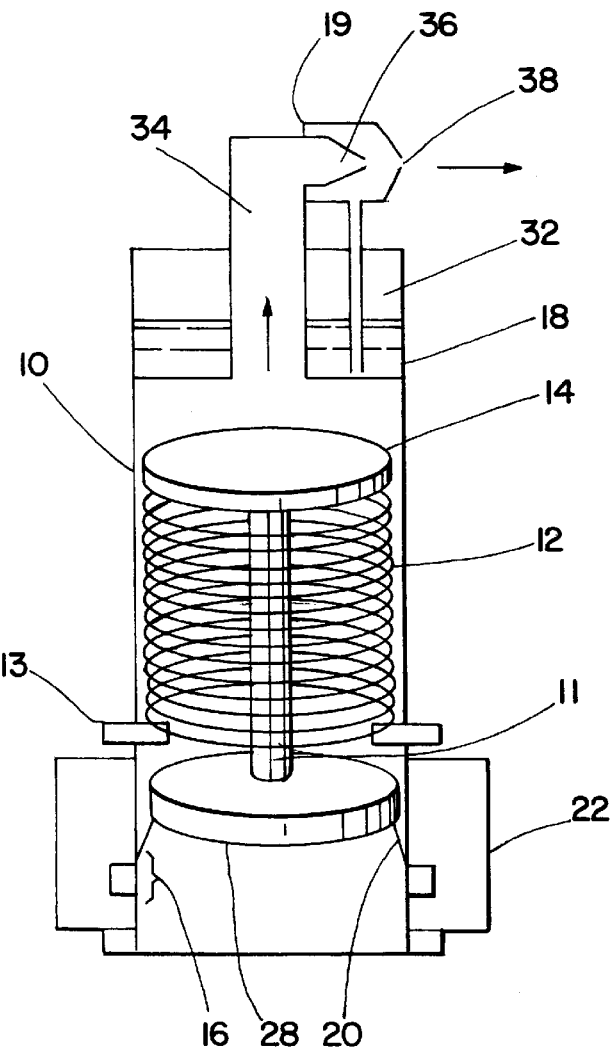
Fig. 1
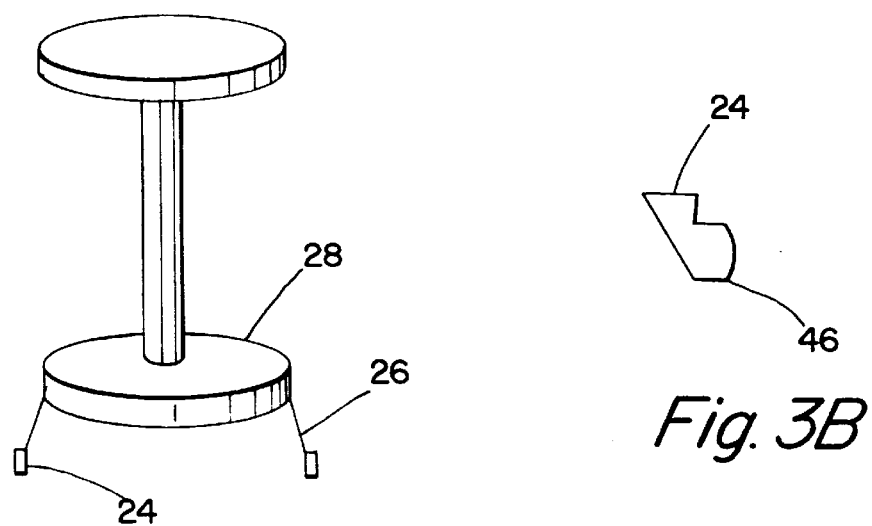
Fig. 3A
Fig. 3B

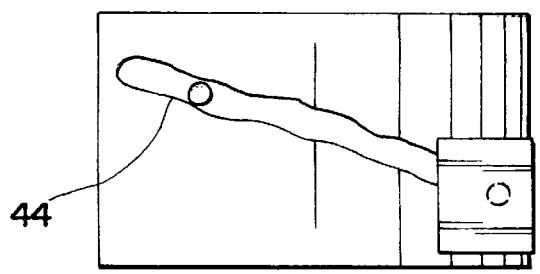
Fig. 4A
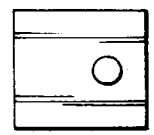
Fig. 4C
Fig. 4B
Fig. 4D
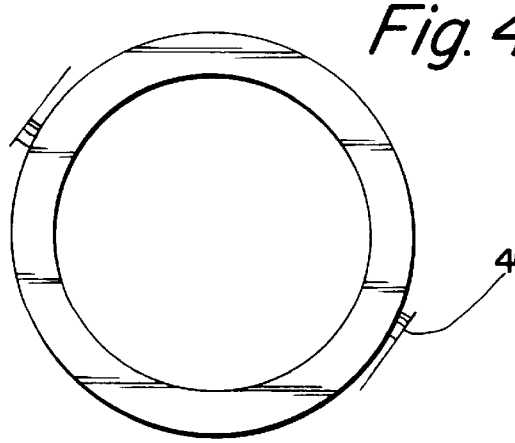
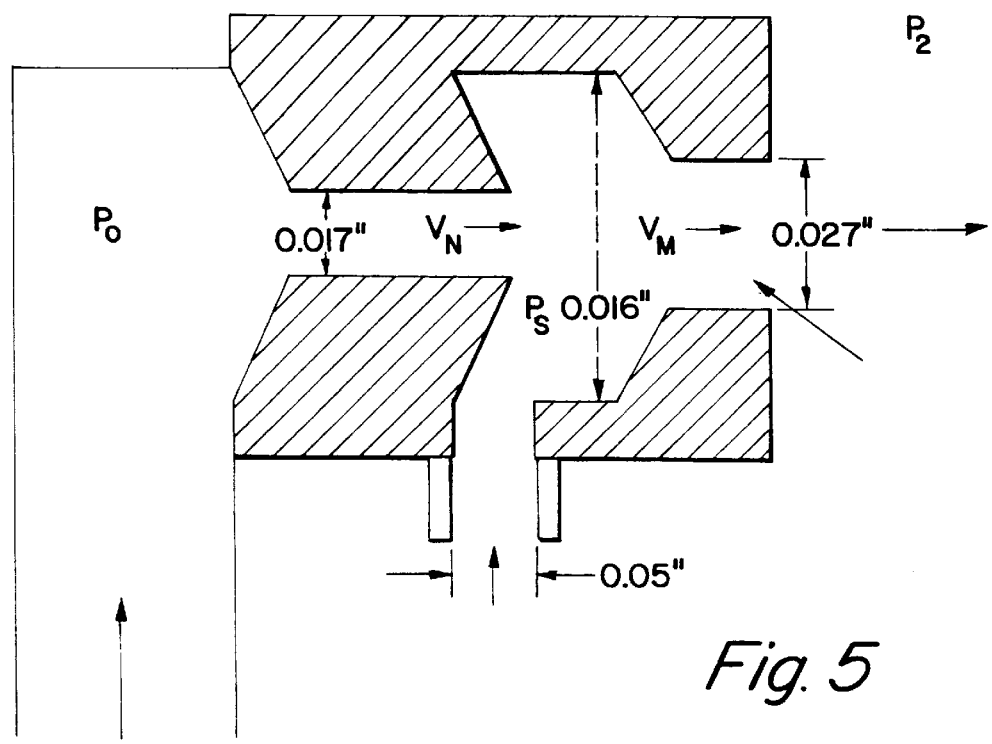
Fig. 5

APPARATUS AND METHOD FOR DELIVERY OF SMALL VOLUMES OF LIQUID

BACKGROUND OF THE INVENTION

1. Field of the Invention

The present invention broadly concerns a system for delivering small predetermined volumes of liquid preparations to the eye or other parts of the mammalian body. The invention has particular application in performing treatments of the eye in a reproducible and reliable manner.

2. Related Art

There is a need for a practical system for delivering small microliter volumes of medicaments accurately to parts of the mammalian body. This is especially the case in the field of ophthalmology. A single drop of current ophthalmic preparations delivers far more volume than the preocular tear film can hold. The excess volume delivered is either drained via the nasolacrimal drainage system, making it available for systemic absorption, or lost as waste over the eyelid margin. However, only limited attempts have been made to develop reliable and practical small volume delivery systems for the ocular surface.

The lacrimal dynamic and pharmacokinetic differences between large (>30 ml) and small (<30 ml) volumes instilled in the eye have been well characterized. Studies in rabbits have determined that the rate of drainage through the nasolacrinal system is directly proportional to the volume of liquid instilled in the eye (Chrai et al., 1973). The normal preocular tear volume is 7.5–10.0 ml. With normal blinking, the volume can be expanded by another 10 ml without overflow (Chrai et al., 1973). Larger volumes of liquid result in a greater preocular drug loss. Increased volume delivered results in both increased drainage of drug via responses such as reflex tearing, further diluting the drug. This means the rate of drug loss actually increases as the volume of drug instilled increases (Chrai et al., 1974).

Studies in rabbits using micropipettes to deliver ophthalmologically-active drugs suggest the desirability of delivering small liquid volumes to the eye in order to minimize systemic effects and maximize local ocular effects. Pilocarpine, a cholinergic parasympathomimetic agent that is used in the treatment of glaucoma, has ocular effects including constriction of the pupil and lowering of the intraocular pressure (IOP). Unwanted systemic effects of this drug may include intestinal spasm, bronchoconstriction, hypotension, and decreased heart rate. Decreasing the dose of pilocarpine administered to the eye allows equivalent absorption of pilocarpine in the aqueous humor of the eye, lowering the IOP, but decreased pilocarpine concentration in the plasma (Patton and Francoeur, 1978; Himmelstein et al., 1978). Other studies have confirmed the existence of this dose effect regarding medication delivered to the eye. For example, Patton found that decreasing the volume instilled in the eye actually increases the fraction of pilocarpine absorbed into the eye from the preocular tear film (Patton, 1977).

Numerous studies in humans further support the desirability of decreasing the volume of liquid pharmaceuticals delivered to the eye. Smaller ocular doses allow maintenance of the ocular therapeutic effects while decreasing or eliminating undesired systemic effects. These smaller doses have been administered using calibrated micropipettes as delivery devices. Using clonidine, an antihypertensive agent, Petursson et al,, (1984) determined that instilling small volumes of 15 $\mu$l to the eye results in separation of the ocular hypotensive effects from the systemic hypotensive effects and equivalent decreases in intraocular pressures as seen with larger volumes. Other authors found that changing the volume of phenylephrine administered to the eye from 32 ml to 10 ml had the same beneficial effect (pupillary dilation) as administering twice the volume, while markedly decreasing systemic absorption and side effects such as increased blood pressure (Brown et. al., 1986). A study in infants using phenylephrine demonstrated that a relatively small volume (8$\mu$l) produced equivalent ocular effects and significantly lowered systemic blood levels when compared to a 30 ml dose (Brown et al., 1987). A study with healthy adult volunteers found no enhancement of pupillary constriction with macrodrop versus microdrop volumes of pilocarpine (File and Patton, 1980). These studies indicate the advantages of using small microliter volumes for ocular solutions; however, the problem of reproducible administration of microvolumes of drug has not been addressed.

While several studies have demonstrated the benefits of using small microliters doses of ophthalmic liquids, the mode of delivery (micropipettes) described is of limited use outside of the laboratory. In particular, micropipetting is not a suitable technique for self-administration by patients. No methods have been described which can accurately and reliably deliver small microliter volumes, are reliable and easily manufactured, and are easily manipulated by non-medical personnel and patients.

Current delivery systems use volumes on the order of 30 $\mu$l and larger because they cannot reliably deliver smaller volumes. Volumes of 30 $\mu$l or more typically result in a large overdose to the eye with systemic effects as the excess drug is absorbed into the circulatory system, and reduced effectiveness and retention time on the ocular surface. The tearing and blinking that accompanies instillation of macrodrops to the eye may cause significant dilution of drug and increased drainage of the drug. Reflex tearing may be in excess of 25 $\mu$l per min. Reduced retention time caused by the activation of tearing which may cause the drug to be washed out and drained from the ocular surface. Blinking that can accompany the instillation of a 30–50 $\mu$l drop in the eye enhances liquid entry into the nasolacrimal drainage system, thereby increasing the rate of drug loss from the preocular tear film.

Current ophthalmic drug delivery devices also present a substantial problem in that the tip can easily come into contact with the eye or surrounding tissue. This creates a path for contaminants to travel between the delivery device and the eye. This is due in part to the fact that patients tend to hold their heads in an awkward position, thus making it more difficult for them to judge where the dispenser bottle is being held relative to the eye. In addition, contact between the dispenser tip and the eye or adnexa may result in clogging of the tip.

Conventional ophthalmic delivery devices typically deliver a single drop of about 30 $\mu$l or more. It is easy to accidentally squeeze the dropper bottle and deliver multiple drops with this dispenser, thus doubling or tripling the dosage with concomitant systemic absorption.

For ophthalmic drugs to be effective, they must be delivered with reasonable reliability to the eye. With current ocular drug delivery systems, it is possible for a patient to miss the eye completely, for example by depositing the drug on the eyelid, and to assume that the drug has been properly delivered. Thus, lack of efficacy may be related to the failure of the delivery system.

The instillation of too large a volume of liquid, 30 $\mu$l or more, to the eye may result in a number of phenomena that reduce the efficiency of drug pharmacokinetics. Reflex tearing results in dilution of the delivered volume, and enhances drainage into the nasolacrimal drainage system. Reflex blinking as a result of macrodrop delivery accentuates the reduction in preocular residence time, and enhances drainage through the nasolacrimal drainage system. Use of macrodrops may further cause discomfort, such as burning and stinging, to the user. Thus, the ability to consistently deliver volumes of liquid medicaments as small as 1 ml is a desirable goal.

SUMMARY OF THE INVENTION

The present invention seeks to address these and other drawbacks inherent in the prior art by providing an ideal volume of delivery to the eye in order to maximize desired local therapeutic effects and minimize systemic effects. In particular, the system employs a gas stream to induce a controlled volume of a liquid into the gas stream and to deliver the liquid in the form of small droplets to a desired site. Of particular interest is the ability of the system to deliver small volumes (i.e., less than about 30 ml) of a liquid as droplets. The droplets are much smaller in size than a normal drop of the liquid. The size of the drop may be generally the size such as is found in an aerosol or mist which may be in the micron range, e.g., 1–5 microns, 10 microns or larger, up to 100 microns, preferably in the range of 10 microns. The diameter of the drops can be calculated using the equation $V=4\pi r^3/3$ where the diameter=2r.

Current drop dispensers are inadequate for small volume delivery, and cannot be made to reliably deliver small microliter volumes. Although small microliter volumes of ophthalmic liquids can be delivered by micropipette, this technique is suitable only for laboratory studies, and is not suitable for self-administration by patients.

In one general aspect the present invention provides a system/apparatus for delivering commonly-used ophthalmic solutions in volumes smaller than amounts delivered through conventional means. The smaller volumes are especially designed to remain within the capacity of the eye to hold the solutions. Exemplary solutions that would benefit from administration by the disclosed system include cholinergic agonists, α-adrenergic agonists, β-adrenergic receptor antagonists and corticosteroids. Cholinergic agonsists, such as pilocarpine, affect the autonomic effector cells innervated by parasympathetic nerves. Pilocarpine's clinical use is restricted to ophthalmic application to induce miosis (pupillary constriction) and decrease the intraocular pressure (IOP). Systemic side effects of pilocarpine may include increased tone and motility of the smooth muscle of the intestine, stimulation of the bronchial smooth muscle resulting in asthmatic attacks, and a marked fall in blood pressure and heart rate. β blockers, such as timolol, block the adrenergic receptors in the sympathetic nervous system. Timolol is used ophthalmologically to decrease IOP in patients with glaucoma. It may be extensively absorbed systemically and result in adverse systemic effects such as decreased blood pressure, decreased heart rate, and bronchoconstriction, and may mask hypoglycemia in patients with diabetes. Clonidine is an α-adrenergic agonist that is used as a topical ophthalmic hypotensive agent. Potential side effects of this drug include hypotension, sedation, bradycardia, and dry nose and/or mouth.

The present invention employs gas induction to deliver small and accurate volumes of liquid in a reproducible and reliable manner. The system does not rely on gravity to separate the liquid for delivery. It relies instead on a preselected volume of gas to both separate and deliver the liquid.

The invention eliminates the problems encountered in droppers which involve adhesion forces including surface tension at the tip, tip diameter, difficulties in use, lack of control of dosage, and contamination.

The pumps in the present invention all operate in response to the flow of a gas. Static forces hold the liquid in place and no liquid is ejected until a threshold velocity of the gas is reached. Once the threshold velocity is reached, liquid is ejected as droplets at sufficient velocity to reach the eye or other body part. The velocity is kept below that which might be harmful or cause discomfort.

Gas induction as in the present invention is superior to direct propulsion or direct ejection of the liquid in two very important ways. First, the gas induction device of the present invention is much less complicated than a direct propulsion device. The gas induction device involves no small moving parts and the delivery and metering may be performed with a piston and requires no complicated valving. A cylinder of gas may also be used. Second, and perhaps more importantly, with the gas induction device the liquid is not ejected until the gas flow reaches a predetermined velocity. This means that the device can bring the gas ejected up to appropriate velocity before liquid will be ejected without an abrupt audible pop or snap. This is extremely important in ophthalmic applications, since experience shows that the sharp audible pop or snap will cause the user to blink and impede the delivery of the liquid to the eye.

In one broad aspect the invention resides in an apparatus which produces a gas stream of a predetermined volume under a preselected pressure; a liquid container; a discharge conduit to deliver a gas stream from the gas container which includes a section to accelerate the gas stream and reduce its static pressure; and an induction conduit or other suitable feeder mechanism to draw liquid from the liquid container into the reduced section for delivery within the gas stream to an eye or other body part.

The gas container is an important feature in that it pressurizes a repeatable volume of gas to a repeatable pressure and volume. The gas container also includes a releasable gas pressurization device and a mechanism for activating release of the pressurizing device.

In a preferred embodiment the gas container comprises a cylinder closed at the top and fitted with a piston capable of compressing gas upon moving toward the top. The piston may have a one-way valve so that gas is not drawn through the pump as the piston is drawn into the cocked position. The piston is connected at its lower end to a cocking member. In a preferred form the cocking member takes the form of two spring loaded lugs or other catches which are attached at their inner ends indirectly to the piston and spring outwardly at their other ends to engage suitable recesses in the cylinder wall or other suitable member.

The piston is capable of being moved by means of a spring interposed between the piston and a fixed position such as a stop attached to the cylinder wall. Thus, the piston may be moved downward within the cylinder, thereby compressing the spring until the catches reach their cocked position. A mechanism is actuated to release the catches, when desired, thereby causing the spring to drive the piston upward and compress gas above the piston.

At least three embodiments are envisioned for inducing liquid into the ejection pathway via a gas. These include eductor pumps, such as jet pumps, venturi nozzles, and metering or paddle wheels. For the purposes of this invention, each of the above is considered a type of "pump" to help induce a liquid into a gas stream and for delivery as droplets to the eye or other body part.

In one embodiment a pump is positioned above the cylinder, and receives compressed gas from the cylinder through a suitable gas passageway. The pump is also connected by a suitable conduit to a reservoir of a liquid drug or other medicament, such that gas passing through the pump draws the liquid from the reservoir, mixes with it, and discharges the liquid as droplets.

The apparatus of the invention delivers volumes with low variability. The apparatus is capable of delivering small volumes on the order of 1 μl to 25 μl consistently. Previous devices such as eye droppers have failed to deliver such small volumes accurately and consistently; they have delivered volumes on the order of 30 ml. The present device, in contrast, is able to deliver volumes of less than 30 ml.

The volume of liquid to be educted may be pre-metered into a chamber. The chamber containing the preselected volume of liquid may be connected to the gas stream from a pump. The preselected volume may be educted and delivered by the gas stream when it has reached the preselected velocity.

It is envisioned that the device of this invention may be modified to deliver one or more unit doses. For the purposes of this invention a unit dose is defined as a volume of a liquid contained in a disposable container. Said container is typically sealed and contains liquid without additional preservatives added.

The apparatus of the invention may be modified in many respects. Thus, the pump may take the form of a jet pump, a venturi, or a paddle wheel. The gas compression source may also take the form of a small cylinder of compressed gas connected through a suitable quick discharge valve to the pump.

A particularly preferred embodiment of the invention is one that is small enough to be held in one hand and carried on one's person. The overall shape may be cylindrical, rectangular, square or molded to fit the hand and may be about 1 to about 3 inches long and about 0.5 to about 1.5 inches in diameter. It may weigh about I to about 12 ounces.

BRIEF DESCRIPTION OF THE DRAWINGS

FIG. 1 is a schematic, longitudinal, cutaway view of one embodiment of the invention revealing internal components of the embodiment.

FIG. 3A is a schematic view of the piston and latch assembly of FIG. 1.

FIG. 3B is a schematic, enlarged side view of a latch shown in FIG. 3A.

FIG. 4A is a schematic, expanded view of one-half of the inner wall surface of the twist ring or sleeve shown in FIG. 1.

FIG. 4B is a schematic, bottom view of the twist ring or sleeve shown in FIG. 1.

FIG. 4C are schematic, top and side views of a device to release the piston shown in FIG. 1.

FIG. 5 is a schematic, side section view of a jet pump shown in FIG. 1.

DESCRIPTION OF ILLUSTRATIVE EMBODIMENTS

Figure 2A:
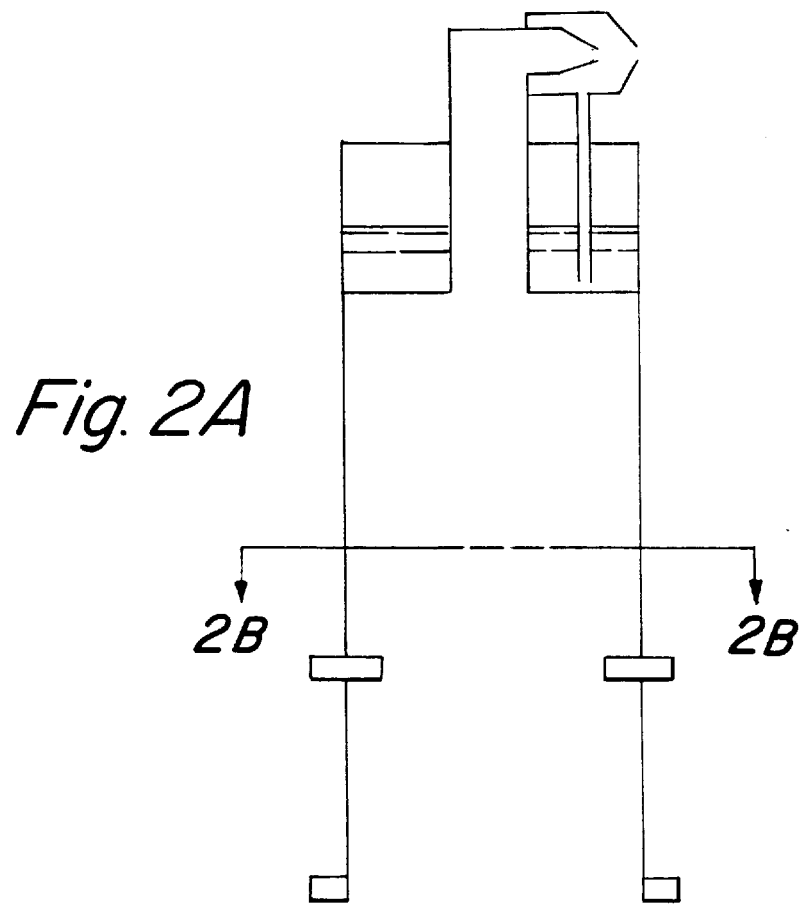
FIG. 2A is a schematic cutaway front view of the housing shown in FIG. 1.
Figure 2B:
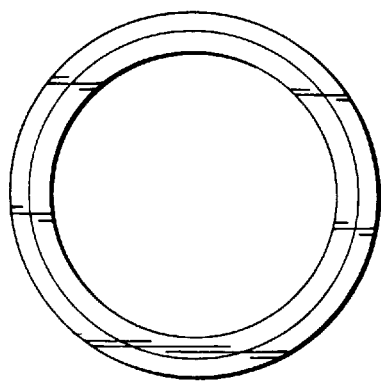
FIG. 2B is a bottom view of the housing.
Figure 2C:
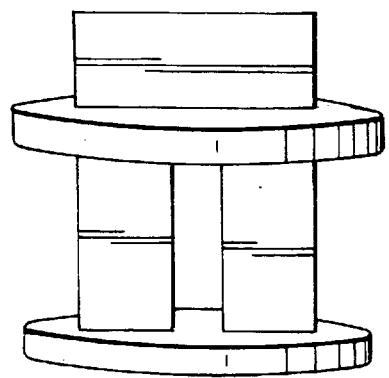
FIG. 2C is a side view of the portion of the housing extending downward from the lines C—C in FIG. 2A.

Two principal techniques have been proposed for delivering small volumes of liquids to the eye. One such technique involves an eye dropper stated to produce a small volume drop of 11 μl (Brown et al., 1985). Another technique involves direct ejection of liquid into the eye via pressurized gas (gas propulsion) (U.S. Pat. No. 3,934,585). However, both of these techniques present difficulties.

The direct ejection technique requires the use of gas which is pressurized in order to propel the ejected liquid with sufficient velocity to reach the eye. However, the direct ejection technique causes ejection of at least some of the liquid before the gas has reached a velocity sufficient to propel the liquid to the surface of the eye. In addition, the direct ejection technique causes an audible pop or snap as the liquid is ejected, resulting in blinking and the potential for consequent misplacement of the liquid.

The dynamic processes involved in creating and delivering a small microliter drop with an eye dropper are often overlooked. Problems with surface tension and adhesive forces between the drop and eye dropper tip make the eye dropper technique inconsistent, unreliable, and unwieldy.

One method of calculating the mass of a normal drop delivered from a device such as an eyedropper is to equate the gravitational forces on the drop with the surface tension of the fluid around the perimeter of the nozzle:

$$m = \frac{\tau \pi d}{g} \qquad (1)$$

where m is the mass of the eyedrop, d is the diameter of the delivery tube, τ is the surface tension of the fluid in question, and g is the acceleration due to gravity (Brown et al., 1985). This equation suggests that reducing d, the diameter of the dropper tube, will consistently reduce the mass of the drop delivered. However, this equation improperly fails to consider factors other than surface tension of the fluid and tube diameter as affecting delivery of small microliter volumes. Because the separation of a drop from the tip of a dropper is a dynamic process, adhesion forces between the drop and the surface of the dropper tip must be considered.

Adhesion forces between the drop and dropper tip prevent the drop from falling from the tip by the force of gravity alone. Equation (1) is assumed to define a break-point at which the drop separates from the tip of the dropper under the influence of gravity. The empirical evidence described in the Brown et al. (1985) publication regarding the tendency of a microdrop (11μl) to stick to the end of a dropper suggests that Equation (1) is oversimplified. A major element that must be considered is that adhesion properties depend on the material comprising the dropper tip. Different materials have different adhesion properties, and drop size will therefore depend on the material used for the dropper tip, as well as on the diameter of the dropper tip.

A better way to understand the process of separation of the drop from the tip of the dropper is to consider the relative forces governing the drop dynamics and ignore the dropper tip effects altogether. This helps to provide the simplest possible picture, while avoiding the introduction of variables such as dropper tip diameter and material. It also provides an accurate estimate of the smallest drop size that can be reliably delivered from the tip of a dropper under the influence of gravity. The relative importance of the surface tension force compared with the gravitational force may be considered by comparing the drop diameter with the capillary constant for water. According to Landau et al. (1987), the capillary constant for a fluid ($\alpha$) may be calculated using the formula:

$$a = \sqrt{\frac{2\tau}{g\rho}} \quad (2)$$

wherein $\rho$ is the mass density of the fluid, $\tau$ is the surface tension of the fluid, and g is the acceleration due to gravity. The units of $\alpha$ are length, and, if the characteristic length dimension (such as the diameter of a sphere) of the unit of fluid in question is small compared with $\alpha$, then the surface tension forces dominate the gravitational forces in the determination of the shape of the unit of fluid. For water, $\tau$ is about 0.072 N/m at 20° C. in contact with air. The corresponding capillary constant for water in air is 0.39 cm. It is important to note that typical eyedroppers deliver a minimum drop size of about 30 μl reliably. The diameter of a 30 μl spherical drop is 0.39 cm, i.e., the same as the capillary constant for water. In contrast, a 10 μl spherical drop of water is about 0.27 cm in diameter and a 1 μl drop is about 0.12 cm in diameter. These diameters are both less than the capillary constant of water. This result strongly suggests that surface tension forces dominate the forces governing these small volumes of liquid that have densities and surface tension forces approaching those of water.

Precise calculations involving the dynamics of a drop on the tip of a dropper are complex. However, since conventional eyedroppers operate ideally with gravity as the only force for shaping and separating the drop from the tip of the dropper, surface tension for 10 μl or smaller volumes is to be expected to be a dominating effect, making gravity delivery of small volumes difficult.

The equality of the diameter of the 30 μl drop and the capillary constant of water is thought to be due to the fact that the separation process of the drop from the tip of a conventional dropper is actually a fluid-fluid separation and not the fluid separating from the tip material of the dropper. What is observed is that the large drop forms a narrow "waist" in the fluid just distal to the tip of the dropper, and the waist becomes progressively narrower until the fluid below the waist separates. This is an instability which only occurs when the characteristic dimension of the fluid volume becomes greater than the capillary constant of the fluid; at this point, the fluid separates from the rest of the fluid and becomes a drop. The remaining fluid on the tip spreads out as a thin layer over the tip of the dropper. This empirical evidence suggests that the adhesion force of the fluid to the tip of the dropper is greater than surface tension force that holds the drop together. Drops that are too small to form this waist under the influence of gravity, drops that are smaller in diameter than the capillary constant of water, will not separate easily from the tip of the dropper with gravity as the only separating force. Thus, volumes smaller than 30 μl have a greater tendency to adhere to the tip of the dropper.

The invention employs a gas such as air, $N_2$, $CO_2$, or any other gas which is inert and medically safe, to induce the delivery of a measured amount of fluid, often aqueous, to the eye. There are several embodiments for this technique, but two method embodiments are described to demonstrate the concept. The first method is a single step induction method. The single step method uses the motive gas for metering and delivering a solution to the eye. The volume of solution delivered to the eye is controlled by the volume and pressure of the motive gas. The second method is a two step induction method. In this method the desired volume of solution is pre-metered into a passage or compartment. The motive gas is forced through the compartment to mix and eject the solution through a nozzle to the eye.

Several apparatus embodiments are described which are multiple dose devices, although they are also capable of operating as unit dose devices. These embodiments implement the overall process of the use of gas induction—i.e., the movement of a measured volume of gas to separate and deliver small preselected volumes of fluid to the eye or other sites. The embodiments shown use a piston and spring for the creation of a momentary high pressure air pulse of a predetermined volume. It will be appreciated, however, that the air pulse may be generated in a variety of ways, and that other gas sources such as pre-pressured cartridges or canisters of $CO_2$, $N_2$ or other non-toxic, non-flammable gases may be used in conjunction with appropriate valving schemes.

A single step induction system is illustrated in FIG. 1. This system employs a measured amount of gas delivered at a given pressure to induce a measured volume of fluid to be pulled into the mixing stream of the pump, become mixed with the air stream, and then ejected from a nozzle.

FIG. 1, FIG. 2, FIG. 3, and FIG. 4 show the principal components of a gas induction delivery system using a jet pump. A venturi or paddle wheel may be substituted for the jet pump without departing from the spirit of the invention. The principal components are:

A main body or housing 10 which houses a spring 12, piston 14, release mechanism and cocking mechanism 16, and solution reservoir 18, and serves as the base for a jet pump 19 (or a venturi). The body 10 in one preferred embodiment is typically about ¾" to 1" in diameter and about 1" to 3" long.

The cocking mechanism 16 enables the piston 14 to be pulled back a predetermined distance, and the spring 12 to be compressed. In this case, the cocking mechanism employs a rotating sleeve 22 which enables the piston to be cocked by twisting the sleeve. The sleeve has a slanted groove shown in FIG. 4A which engages a catch mechanism 20 on the bottom of the piston. The sleeve is typically about ⅛" to ¼" larger in diameter than the main body and about ½" high. The catch mechanism shown in FIG. 3 comprises two catches 24 spring loaded by metallic spurs 26 attached to a centralizing disk 28. It will be apparent that the stroke of the piston may be varied by varying the position of the catches.

The reservoir 18 is preferably close to the jet pump 19, and contains a solution liquid. The reservoir 18 has a feeder tube 32 extending through the top of the reservoir down to the bottom to enable the liquid to be pulled up into the jet pump for delivery. In this case the reservoir 18 is doughnut shaped to permit a passage 34 to allow air to flow through the middle from above piston 14 to drive the jet pump 19 affixed to the top of housing 10. The outer diameter of the reservoir 18 is the diameter of the main housing 10, and there is an inner diameter to allow the air tube 34 to pass through the middle.

The jet pump 19 converts pressurized gas from passageway 34 into suction, and pulls solution liquid from the reservoir 18 up the feeder tube 32 into the pump, and then ejects it into the eye. The jet pump here comprises an inner nozzle 36 and an outer nozzle 38. The inner nozzle 36 is called the jet, and the outer nozzle 38 is called the diffuser. The diameter of the diffuser is preferably larger than the diameter of the jet. The operation of the jet pump for this system is explained in more detail below. The jet pump may be cylindrical in shape.

The piston 14 is a free-sliding piston which is sealed against the housing 10, and connected to a shaft 11 and disk 28 for guiding the piston. The guiding mechanism is connected to the cocking mechanism 16.

The spring 12 is positioned between the piston 14 and one or more spring stops 13. The spring is also centered around the shaft 11. The spring is compressed by action of the cocking mechanism as it is drawn with piston 14 by the cocking mechanism. The cocking mechanism includes a sleeve 22 which has two opposed, inclined grooves or tracks 44. The sleeve typically may be larger than the housing. It also includes a pair of spring loaded latches or catches 24 which snap into the grooves when the piston 14 moves downward against the spring 12. The catches 24 are biased outward by spring members attached to the disk 28. Rotation of the sleeve causes the catches 24 to ride down along the grooves, until the catches enter deeper recesses or holes in the sleeve 22. They remain cocked in this position until their release by release mechanism 46. The release mechanism 46 may comprise elongated buttons or rods 48 which are positioned on the sleeve 22 opposite the catches 24 when in their cocked position. Simply pushing or pressing the buttons or rods 48 inward displaces the catches 24 inward and out of the grooves 44, thereby freeing the spring to thrust the piston upward. Upward movement of the piston compresses and drives a selected volume of gas through the passageway 34 and thence the jet pump. This, in turn, draws a selected volume of liquid from the reservoir 18 through the feeder tube 32 and into the gas stream. The liquid mixes with the gas and jets through the outer nozzle 38.

A drawing of the housing with the piston and twist ring removed is shown for clarity in FIG. 2A. The piston and the locking and release mechanisms are shown in FIG. 3A and FIG. 3B. The twist ring is shown in FIG. 4 with a slanted slot cut on the inner surface of the ring. There are two slots on the twist ring, one on each side of the twist ring.

EXAMPLE 1

Consideration of the jet pump using steady incompressible flow and treating the fluid mixing empirically yields a straightforward analysis (Jumpeter, 1986; Gosline et al., 1937). However, these analyses are incomplete for this application because they do not provide expressions that give explicit transfer volumes for motive and suction fluids with dissimilar densities. Therefore, the inventors present an analysis here that gives the transfer of a specific volume of suction fluid for a give volume of motive fluid where the densities of the two fluids are not equal. A detailed drawing of an example of a jet pump is shown in FIG. 5 with representative dimensions. For the sake of simplicity, the flow of the motive gas and the suction fluid may be approximated by steady incompressible flow, hence, that Bernoulli's equation may be used for the conservation of momentum flow:

$$\frac{P}{\rho} + \frac{V^2}{2} = H \tag{3}$$

where H is a constant, P is pressure, $\rho$ is mass density of the fluid, and V is the fluid velocity (Fox and McDonald, 1992). The constant, H, on the right hand side of the equation will be referred to as the head or stagnation pressure normalized to the density of the gas or fluid. The stagnation pressure is a normalized quantity composed of the static pressure P and the dynamic pressure $\rho V^2/2$. These quantities are normalized to the fluid density for simplicity. This equation is consistent for a consistent set of units, such as MKS units. For the jet pump shown in FIG. 5, it is important to describe the operation of the device so that it is clear that a premetered volume of gas induces a preselected amount of fluid to be delivered.

The equation for the head pressure, $h_I$, of the motive gas is:

$$h_1 = \frac{P_1}{\rho_1} + \frac{V_1^2}{2} \tag{4}$$

where $V_1$ can be considered to be zero before the fluid enters the nozzle. The following equation relates the nozzle velocity to the head pressure, $h_I$.

$$h_1 = \frac{P_s}{\rho_1} + \frac{V_N^2}{2} \tag{5}$$

where $P_s$ is the suction pressure, and $V_N$ is the nozzle velocity. The equation for the velocity and pressure in the diffuser section of the pump, exiting into pressure $P_2$, usually atmospheric pressure, is:

$$\frac{P_2}{\rho_2} = \frac{P_s}{\rho_2} + \frac{V_M^2}{2} \tag{5A}$$

Where $V_M$ is the velocity of the mixture of motive gas and suction fluid in the diffuse before exiting the pump. Equations 5 and 5A establish the relationship between the velocities at the nozzle and in the diffuser, and the motive, suction, and exit pressures, $P_1$, $P_s$, and $P_2$, respectively. These equations may be combined and provide an expression for the relative ability of the jet pump to eject the suction fluid. This relative pumping ability is expressed as the head ratio, $R_H$, expressed in terms of the pressures at the ports of the pump:

$$R_H = \frac{(P_1 - P_S)\rho_2}{(P_2 - P_S)\rho_1} \tag{6}$$

where $P_1$ is the piston pressure, $P_2$ is the discharge pressure at the output of the pump, $P_s$ is the suction pressure, $\rho_2$ is the mass density of the mixture of the motive gas and suction fluid, and $R_H$ is the head ratio for the jet pump corrected for the mass densities of the motive gas and the effective density of the motive gas mixed with the suction fluid. The density of the fluid/gas mixture is difficult to determine a priori. This mixture, or average density, depends strongly on the properties of the solution fluid, and the details of the pump. One factor, for example that changes the relative fraction of solution fluid induced into the jet pump is the length of the feeder tube. The mixing ratio, r, may be defined as the average volume of ejected suction fluid, $V_{suction}$, to the average volume of motive gas initially displaced by the piston, $V_{piston}$:

$$r = \frac{V_{suction}}{V_{piston}} \quad (7)$$

The average mass density of the ejected mixture may be computed by finding the total mass of the ejected mixture and dividing by the total volume of the ejected mixture (at the exit or atmospheric pressure). This may be expressed in terms of the motive gas density, the suction fluid (solution) density, and the mixing ratio as:

$$\rho_2 = \frac{\rho_1 + r\rho_{suction}}{1+R} \quad (8)$$

where $\rho_{suction}$ is the density of the suction fluid.

Empirical measurements show that for moderate displacements of air (i.e., 2–5ml), a suction fluid of water, and a short feeder tube, the relative volume of solution ejected to the volume of motive gas displaced is approximately 1.4 to 1.8 $\mu$l ml. If the average value of these ratios is used, the inventors have 1.6 $\mu$l/ml, and an average density for $\rho_2$ of 2.8 kg/m$^3$. Thus, a predetermined amount of suction fluid may be delivered by setting the pressure and the amount of motive gas to be displaced. This may be calculated by knowing the relative velocities of the motive fluid to the mixed fluid stream and may be calculated from $R_H$ as follows:

$$V_M = \frac{V_N}{\sqrt{R_H}} \quad (9)$$

where $V_M$ is the velocity of the mixed fluids that are ejected, and by using conservation of momentum the inventors can write the total mass of suction fluid transferred in terms of the total mass of the motive gas:

$$\rho_{suction} V_{suction} = \rho_1 V_{piston}\left(\frac{V_N}{V_M} - 1\right) \quad (10)$$

This equation show that the ejection velocity must be reduced compared with $V_N$, since the combined mass of the suction fluid and motive gas are greater than the mass of motive gas alone. Equation 10 can be divided by $V_{piston}$ and $\rho_{suction}$ to give an expression in terms of the mixing ratio, r. Furthermore, $V_N/V_M=\sqrt{R_H}$ can be substituted into equation 10 to obtain:

$$r = \varepsilon \frac{\rho_1}{\rho_{suction}}\left(\sqrt{R_H} - 1\right) \quad (11)$$

Equation (11) shows that the volume of the suction fluid, $V_{suction}$ transferred is controlled through the mixing ratio, r, by the total volume and density of the motive fluid, and the head ratio, $R_H$ at which it is delivered. Thus it is clear from equation 11 that the total volume of fluid, $V_{suction}$, ejected can be controlled by controlling the anount of gas, $V_{piston}$, at a known density and pressure that is forced through the nozzle. Mixing and turbulence losses have been included by adding an empirically determined efficiency, $\epsilon$. (19). Although equation 11 appears to be an expression for r in terms of other variables, $R_H$ depends on r through the term $\rho_2$. If $\rho_2$ is replaced in the expression for $R_H$ by equation 8, and r is solved for in terms of all the other variables, a 3rd order polynomial in r is obtained, the first real root of which is the physically meaningful value for r. The expression is:

$$r^3 + Ar^2 + Br + C + 0 \quad (12)$$

$$A = 1 + 2\epsilon\alpha \quad (12a)$$

$$B = (\alpha^2\epsilon^2 + \alpha\epsilon - P_H\alpha\epsilon^2) \quad (12b)$$

$$C = \alpha^2\epsilon^2(1 - P_H) \quad (12c)$$

$$\alpha = \frac{\rho_1}{\rho_{suction}} \quad (12d)$$

$$P_H = \frac{P_1 - P_s}{P_2 - P_s} \quad (12e)$$

The real root of this equation will give the mixing ratio if the motive, suction, and discharge pressures, the density of the motive and suction fluids, and the empirical efficiency coefficient are known. The mixing ratio can then be determined. This equation is limited in its predictive ability because it cannot be used until $\epsilon$ is determined. However, it is useful because it gives the mixing ratio, r, as a function of all of the other parameters of the jet pump. This equation is essential for determining how the mixing ratio changes when other variable such as motive gas pressure or density are changed.

Although velocity does not appear explicitly in equation 12, it is clear that the pump action is caused by the flow of gas through the inner and outer nozzles of the jet pump. No suction fluid will be ejected until the velocity is high enough to create sufficient suction to overcome the forces holding the suction fluid in the feeder tube.

It is important to note that equation 12 cannot be used a prioi to determine the exact delivery volumes. There are a number of empirical factors that cannot be determined except by measurement. First, the mixing ratio, r, and the overall efficiency factor, $\epsilon$, are not known and must be determined empirically. In addition, the suction pressure, $P_s$, is determined by surface adhesion forces and surface tension forces that are difficult to calculate in advance. Therefore, these equations cannot be used to predict the exact volume delivery of a jet pump for the purpose of small volume delivery. However these equations are useful for determining the scaling behavior of the pump assembly once these factors have been determined. Changes in the delivered volume of fluid, $V_{suction}$, may be determined from changes in the volume of the piston, the pressure of the spring, or the density of the motive gas used.

Test data indicate that an early prototypic embodiment similar to that in FIG. 5 can deliver reliably a 5$\mu$l volume to a pre-determined target, such as the eye, with a 20% standard deviation from the average. The data are shown in following Table 1. In this test the feeder tube was about 2" long and the fluid level in the reservoir was about ¾" below the jet pump. Thus, the total hydrostatic head against which the pump had to work was about ¾". The volume of fluid delivered was determined using a petri dish containing a small wad of dry cotton on a precision scale. The nozzle was placed in close proximity to the cotton and then discharged into the cotton. The difference in the weight of the petri dish was measured before and after the discharge. The suction fluid in this case was tap water which has a known density of $10^3$ kg/m$^3$. The temperature of the water was approximately room temperature, estimated to be about 23° C. The scale was a Mettler-Toledo Model AG245 with a 10 $\mu$g accuracy. A change in weight of 1000 $\mu$g (1 mg) corresponded to a 1 $\mu$l delivery to the cotton. The piston used was that in a standard 10 cc polyethylene syringe, and the pressure was applied by the thumb. Different volumes of air (2.5, 5.0 and 7.0 ml) were displaced from the syringe by its piston. The delivery was accomplished by a quick, sharp push to the syringe piston. The same operator was used for all of the test data shown here. Since the motive piston was pushed by hand, variability was probably introduced into these results; a spring or other mechanical means provides more repeatable motive pressure.

Table 1 shows the volumes of suction fluid that were delivered by the above device by ejecting different quantities of air from the syringe. The data in the first or left hand column show the quantities of suction fluid (tap water) that were delivered by 2.5 ml of air displaced by the syringe in 21 different trials. The second and third columns show similar results, when the syringe delivered 5.0 ml and 7.5 ml volumes of air, respectively. The data in Table 1 below show that as little as 2 $\mu$l average volume of suction fluid may be delivered, with a standard deviation of about 22% of the mean. The maximum volume was 2.9 $\mu$l, while the minimum as 1.3 $\mu$l. The ratio of maximum to minimum volume delivered was about 2, and it was fairly consistent for all of the test data taken so far. A further important feature of this data is that the mixing ratio of total suction fluid volume to motive gas volume changes noticeably from the 2.5 ml of motive gas, to the 7.5 ml of motive gas used. The mixing ratio changes from 0.8 $\mu$l/ml for 2.5 ml of motive gas to 1.45 $\mu$l/ml for 7.5 ml of motive gas, respectively. This is about a 45% change in the mixing ratio from the minimum volume of gas used to the maximum volume used, which corresponds to about a 3-to-1 change in the motive volume of gas.

TABLE 1

Volumes of Fluid Delivered by Different Volumes of Motive Air

| Trial # | 2.5 ml air | Trial # | 5 ml air | Trial # | 7.5 ml air |
| --- | --- | --- | --- | --- | --- |
| 1 | 2.0 | 1 | 5.0 | 1 | 9.5 |
| 2 | 1.5 | 2 | 5.5 | 2 | 9.5 |
| 3 | 1.7 | 3 | 5.7 | 3 | 9.0 |
| 4 | 1.7 | 4 | 5.9 | 4 | 9.5 |
| 5 | 1.8 | 5 | 6.4 | 5 | 9.3 |
| 6 | 1.5 | 6 | 5.8 | 6 | 8.6 |
| 7 | 2.7 | 7 | 6.2 | 7 | 9.5 |
| 8 | 1.9 | 8 | 7.0 | 8 | 11.7 |
| 9 | 1.3 | 9 | 7.1 | 9 | 12.4 |
| 10 | 2.7 | 10 | 5.2 | 10 | 11.4 |
| 11 | 2.8 | 11 | 6.7 | 11 | 10.8 |
| 12 | 2.9 | 12 | 6.6 | 12 | 12.3 |
| 13 | 2.3 | 13 | 5.0 | 13 | 11.3 |
| 14 | 2.2 | 14 | 6.0 | 14 | 10.0 |
| 15 | 2.2 | 15 | 5.0 | 15 | 11.6 |
| 16 | 2.0 | 16 | 5.7 | 16 | 10.9 |
| 17 | 2.4 | 17 | 5.6 | 17 | 13.8 |
| 18 | 2.2 | 18 | 4.7 | 18 | 10.9 |
| 19 | 1.8 | 19 | 5.5 | 19 | 9.5 |
| 20 | 1.5 | 20 | 5.0 | 20 | 11.6 |
| 21 | 1.8 | 21 | 7.0 | 21 | 11.6 |
| 22 | 1.4 | 22 | 5.9 | 22 | 10.5 |
|  |  | 23 | 6.4 | 23 | 10.4 |

TABLE 1-continued

Volumes of Fluid Delivered by Different Volumes of Motive Air

| Trial # | 2.5 ml air | Trial # | 5 ml air | Trial # | 7.5 ml air |
| --- | --- | --- | --- | --- | --- |
| Average | 2.0 | 24 | 5.8 | 24 | 13.0 |
| Std Dev | 0.5 | 25 | 5.9 | 25 | 12.7 |
| Max | 2.9 | 26 | 6.0 | 26 | 12.5 |
| Min | 1.3 | 27 | 6.0 | 27 | 11.1 |
|  |  | 28 | 6.2 | 28 | 10.2 |
|  |  | 29 | 7.1 | 29 | 12.2 |
|  |  | 30 | 6.5 | 30 | 10.9 |
|  |  | 31 | 6.6 | 31 | 10.9 |
|  |  | 32 | 6.3 | 32 | 11.8 |
|  |  | 33 | 6.0 | 33 | 10.5 |
|  |  | 34 | 5.6 | 34 | 10.4 |
|  |  | 35 | 6.0 | 35 | 8.9 |
|  |  | 36 | 6.6 | 36 | 11.6 |
|  |  | 37 | 6.1 | 37 | 9.1 |
|  |  | 38 | 5.9 | 38 | 13.4 |
|  |  | 39 | 5.8 | 39 | 11.3 |
|  |  | 40 | 6.0 | 40 | 11.9 |
|  |  |  |  | 41 | 9.8 |
|  |  | Average | 6.0 | 42 | 10.4 |
|  |  | Std Dev | 0.6 | 43 | 10.4 |
|  |  | Max | 7.1 | 44 | 12.5 |
|  |  | Min | 4.7 |  |  |
|  |  |  |  | Average | 10.9 |
|  |  |  |  | Std Dev | 1.3 |
|  |  |  |  | Max | 13.8 |
|  |  |  |  | Min | 8.6 |

Because the amounts of liquid measured were very small (in some cases less than 2 $\mu$l), evaporation of the liquid from the target on the scale was potentially a significant factor in the measurement. The evaporation rate was proportional to the amount of liquid delivered to the cotton; smaller delivery volumes had a smaller rate of evaporation. In order to minimize the effect of evaporation, the readings were taken as quickly as possible after the delivery to the cotton, 10 to 20 sec, and efforts were made to keep the time between delivery and the measurement of the weight change constant. The determining factor on the measurement time was the time for the scale to stabilize. The cotton target was changed after 5 to 10 deliveries. The evaporation of the liquid from the target ranged from less than about ½ mg per min for a fresh target to about 3 mg/min for the larger volume deliveries after about 10 deliveries. The large evaporation rates were only observed with multiple deliveries of water to the cotton at relatively high volume (i.e., 10 $\mu$l). Overall, the evaporation rates were not considered to be significant for the measurements made.

Table 2 below shows data taken with a similar early prototypic jet pump and motive piston. The important differences were that the feeder tube was shortened to about ¾", and the liquid was about ¼" below the jet pump. The experimental design was otherwise the same as that for the data in Table 1. In these trials different volumes of motive air (1.0, 2.0, 2.5 and 4.0 ml) were used to deliver tap water as a treating liquid. It may be seen that the standard deviations for this data are all very close to about 20% of the average volume delivered, except for the 4 ml of air delivery which had a standard deviation of about 15% of the average value. More importantly, the mixing ratio computed using the average ranged from a minimum of 1.4 $\mu$l/ml to 1.8 $\mu$l/ml. This is change of only 14% over the entire range of volumes delivered. The ratio of the change of motive gas volumes is 4 ml/1 ml or a range of 4-to −1.

TABLE 2

Different Volumes of Liquid Delivered by Different Volumes of Motive Air

| Trial # | 1.0 ml air | Trial # | 2.0 ml air | Trial # | 2.5 ml air | Trial # | 4.0 ml air |
|---|---|---|---|---|---|---|---|
| 1 | 1.40 | 1 | 2.60 | 1 | 4.62 | 1 | 7.40 |
| 2 | 1.36 | 2 | 2.74 | 2 | 3.52 | 2 | 10.00 |
| 3 | 1.16 | 3 | 2.45 | 3 | 3.06 | 3 | 7.06 |
| 4 | 1.40 | 4 | 2.90 | 4 | 4.14 | 4 | 6.50 |
| 5 | 1.08 | 5 | 3.36 | 5 | 4.50 | 5 | 6.60 |
| 6 | 1.40 | 6 | 3.60 | 6 | 4.30 | 6 | 6.70 |
| 7 | 1.08 | 7 | 3.30 | 7 | 3.81 | 7 | 6.30 |
| 8 | 1.35 | 8 | 2.36 | 8 | 5.54 | 8 | 8.11 |
| 9 | 1.40 | 9 | 2.10 | 9 | 4.05 | 9 | 9.30 |
| 10 | 1.65 | 10 | 2.00 | 10 | 3.85 | 10 | 6.84 |
| 11 | 0.95 | 11 | 3.96 | 11 | 3.58 | '1 | 7.50 |
| 12 | 1.05 | 12 | 2.00 | 12 | 4.55 | 12 | 7.00 |
| 13 | 1.35 | 13 | 2.80 | 13 | 4.21 | 13 | 5.20 |
| 14 | 1.82 | 14 | 3.10 | 14 | 3.68 | 14 | 6.88 |
| 15 | 1.55 | 15 | 2.60 | 15 | 5.33 | 15 | 6.50 |
| 16 | 1.18 | 16 | 4.00 | 16 | 6.56 | 16 | 6.67 |
| 17 | 1.37 | 17 | 3.20 | 17 | 3.80 | 17 | 8.44 |
| 18 | 1.04 | 18 | 2.40 | 18 | 4.20 | 18 | 7.44 |
| 19 | 1.28 | 19 | 2.30 | 19 | 4.80 | 19 | 7.67 |
| 20 | 1.36 | 20 | 3.00 | 20 | 3.01 | 20 | 6.19 |
| 21 | 1.50 | 21 | 4.20 | 21 | 4.26 | 21 | 8.00 |
| 22 | 1.69 | 22 | 4.20 | 22 | 4.21 | | |
| 23 | 1.10 | 23 | 3.60 | 23 | 4.09 | | |
| 24 | 1.84 | 24 | 3.40 | 24 | 4.20 | Average | 7.25 |
| 25 | 1.36 | 25 | 3.15 | | | Std Dev | 1.06 |
| 26 | 1.50 | 26 | 3.20 | | | Max | 10.00 |
| 27 | 2.10 | 27 | 3.30 | Average | 4.24 | Min | 5.20 |
| 28 | 1.60 | 28 | 2.80 | Std Dev | 0.75 | | |
| 29 | 1.40 | 29 | 2.40 | Max | 6.56 | | |
| 30 | 1.24 | 30 | 3.60 | Min | 3.01 | | |
| 31 | 1.72 | 31 | 3.70 | | | | |
| | | 32 | 4.30 | | | | |
| Average | 1.40 | | | | | | |
| Std Dev | 0.26 | Average | 3.08 | | | | |
| Max | 2.10 | Std Dev | 0.65 | | | | |
| Min | 0.95 | Max | 4.30 | | | | |
| | | Min | 2.00 | | | | |

The fact that the range of mixing ratios was much smaller for the data in Table 2 as opposed to that in Table 1, over an even larger range of motive gas volumes, is evidence that control of the amount of fluid delivered by this method was achieved. By determining the parameters needed to produce a stable mixing ratio, as was accomplished here, the amount of motive gas needed to deliver a preselected volume of fluid may be determined. A longer feeder tube requires more gas displacement to achieve the same relative mixture of the fluid to the motive gas. For a longer feeder tube (i.e., one of about 2" in length), the mixture depends strongly on the amount of gas displaced. A shorter feeder tube (about ½" in length) shows only a very slight dependence of the mixing ratio to the total gas displaced for the range of 1 to 4 ml of air. Another feature of the mixing ratio of the long feeder tube is that for large gas displacements, it asymptotes to a value that approaches the mixing ratio for the short tube. This is due to the need to overcome the inertia of the liquid in the feeder tube. The shorter the feeder tube, the less the inertia that needs to be overcome. When a larger volume of motive gas is used, the liquid approaches a more constant steady flow, resulting in a more consistent mixing ratio.

In order to estimate efficiency of the jet pump, and to predict the influence of changes in the configuration of the feeder tube, there is a need to be able to calculate the total effective head ($H_s$) against which the jet pump must pull in order to produce a positive flow into the pump. The forces have the following components: gravity, static pressure, and viscosity. The resulting equation for the suction pressure, $P_s$, is:

$$P = P_s g z + P_{stat} + V_s K \qquad (13)$$

where g is the pull of gravity, $\rho_s$ is the density of the suction fluid, z is the height of the jet pump above the fluid level, $P_{stat}$ is the pressure corresponding to static force such as surface tension, $V_s$ is the velocity of the fluid in the tube leading from the reservoir to the jet pump, and K is a constant computed from the absolute viscosity of the fluid at the typical temperatures that are expected and the dimensions of the feeder tube. Because the volume flow rates are so low ($10^{-9} m^3/s$) for the suction fluid, the viscosity term for aqueous fluids with properties similar to water is negligibly small (0.5 Pa) even for small diameter feeder tubes, in this case 0.05" diameter. The flow for aqueous solutions is laminar, again because of the low volume flow of the suction fluid. The gravity pressure is 120 Pa for ½" of total lift (½" feeder tube). The static pressure term was estimated from the amount of fluid that remained in the feed tube when the tube was held free in the air vertically and was about ⅜" which corresponds to a value of about 90 Pa. Thus, the value of 210 Pa was used as an estimate for the overall suction head.

Using equation 12, the measured mixing ratio, and estimating the relative head ratio $R_H$ corrected for the mass densities of the mixture and motive gas, one can estimate the relative efficiency, $\epsilon$, of the jet pump. The over pressure, $P_1$, which is the pressure in excess of atmospheric pressure, in the piston is estimated at between 6 kPa and 10 kPa (ie., 6–10% of one atmosphere), assuming about 0.20 to 0.25 pounds of force applied to the piston. The suction pressure, $P_s$, is estimated to be about 210 Pa. Corresponding $R_H$ is between 60 and 100, which gives an efficiency, $\epsilon$, in the range of 0.14 to 0.19 using equation 12. Since the motive fluid (gas) is much less dense and more compressible than the suction fluid, it is not expected that the efficiency will be much higher than this for a jet pump.

Certain approximations have been made but are not believed to significantly affect accuracy. Thus, an assumed steady flow discounted the inertia of the motive gas as well as the suction fluid. This is a better approximation for the short tube than for the longer tube. Since the suction fluid is nearly incompressible, the entire suction tube must be set in motion to feed the pump, hence the inertia of interest is the inertia of the entire fluid in the feeder tube. The longer the feeder tube, the greater the inertia. The constancy of the mixing ratio of the short tube for the various displacements of air suggests that the inertia is not a large factor, and hence the steady flow approximation is accurate for the inventors' calculations.

Figure 6A:
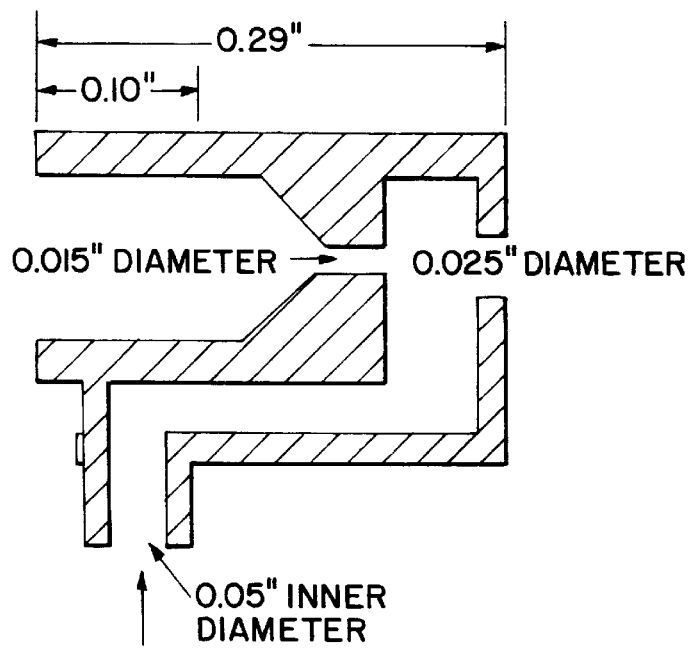
FIG. 6 shows schematically a variation of the liquid reservoir and jet pump of FIG. 1.
Figure 6C:
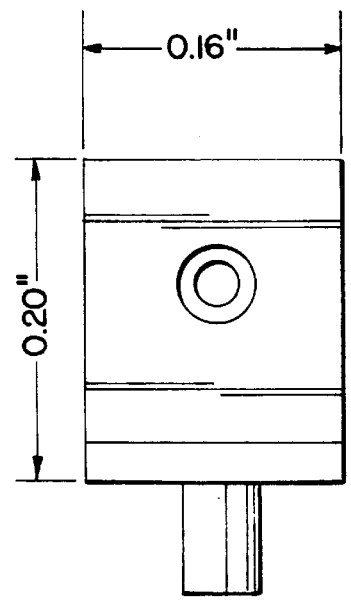
Figure 6B:
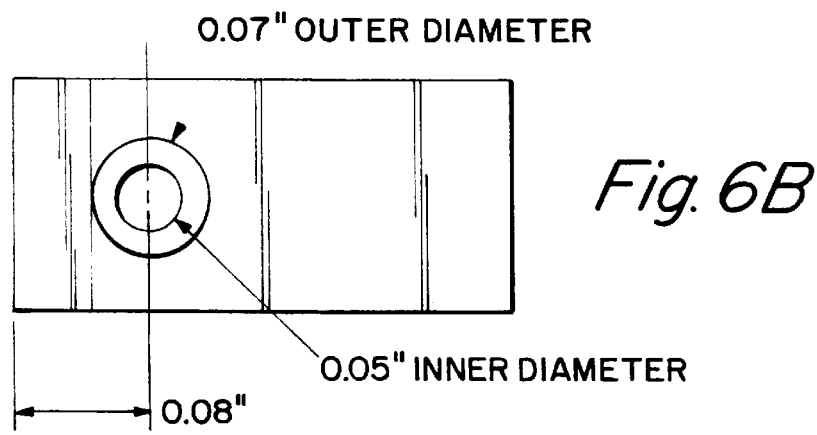

The pump is an operational element of this invention, and may comprise a jet pump, a venturi or a paddle wheel. FIG. 6 shows a simple design of a jet pump. This pump only has three parts to assemble, including the feeder tube for the suction fluid. One aspect of this pump design is that the housing for the motive jet, the pressure inlet, and the exit nozzle are all molded from the same piece. The small holes may either be molded or drilled quite easily. This pump may be made from plastic, such as polystyrene, polyvinyl chloride, metal, or any rigid, castable, or moldable (epoxy, silicone rubber, polyurethane) material that is impervious to fluids such as water. Although the outer shape is shown as rectangular here, it does not have any effect on the performance of the pump, therefore the most convenient outer shape may be made. There are no complicated moldings or assemblies required for this unit, and is therefore low cost. The dimensions shown in FIG. 6 are representative of typical dimensions for a hand-held unit for self administration and may be varied to suit the application. The assembly described also is of very low cost in both materials and construction.

Figure 7:
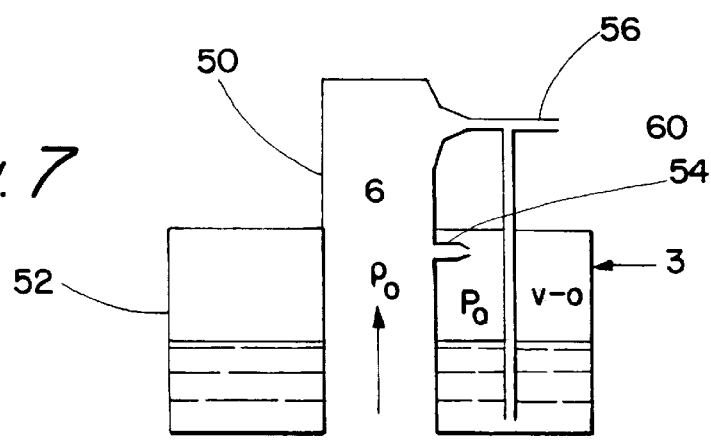
FIG. 7 is a schematic diagram of a venturi and feeder tube portion of an embodiment of the invention otherwise similar to that in FIG. 1.

Another one step method that may be used for gas induction employs a venturi as a pump. It is envisioned that the stagnation pressure of the motive gas provides a means to drive the fluid from the reservoir to the passage. It is important to note that the reservoir containing the solution must be momentarily pressurized by the action of the piston, otherwise, the stored solution will not be ejected into the stream of the gas flow. FIG. 7 shows an example of how this may be implemented. The passageway 50 that provides the head for the motive air is also connected to the reservoir 52 containing the solution. The piston and the locking mechanisms are essentially the same as in the previous embodiment. However, the housing shown in FIG. 7 now has an additional passage (component 54 in FIG. 7) from the pressurized gas tube 50 into the solution reservoir 52 to provide the static pressure which pushes against the moving stream in the venturi 56. A very small feeder tube 60 connects from the reservoir to the venturi 56, and the reduced static pressure in the venturi 56 causes a pressure differential which forces the suction fluid to flow from the reservoir to the gas passage at a rate set by the driving pressure of the piston, the known fluid properties of the solution, and the diameter of the feeder tube 60 and the gas tube.

The solution is moved by the difference in pressure created when the flow velocity is increased above zero. Since the reservoir that contains the solution is at the pressure induced by the piston, that is the stagnation pressure, and the velocity is zero in this chamber, there will be a pressure difference that drives the solution up and through the tube 60 into the air flow. $P_s$ at the venturi 56 will be smaller than $P_o$ in the reservoir. If the gas velocity in 6 (FIG. 7) is not negligibly small, the reservoir will be pressurized to a pressure $<P_o$ but $>P_s$. The result will be that higher gas velocity will be required before the fluid is educted.

Figure 8:
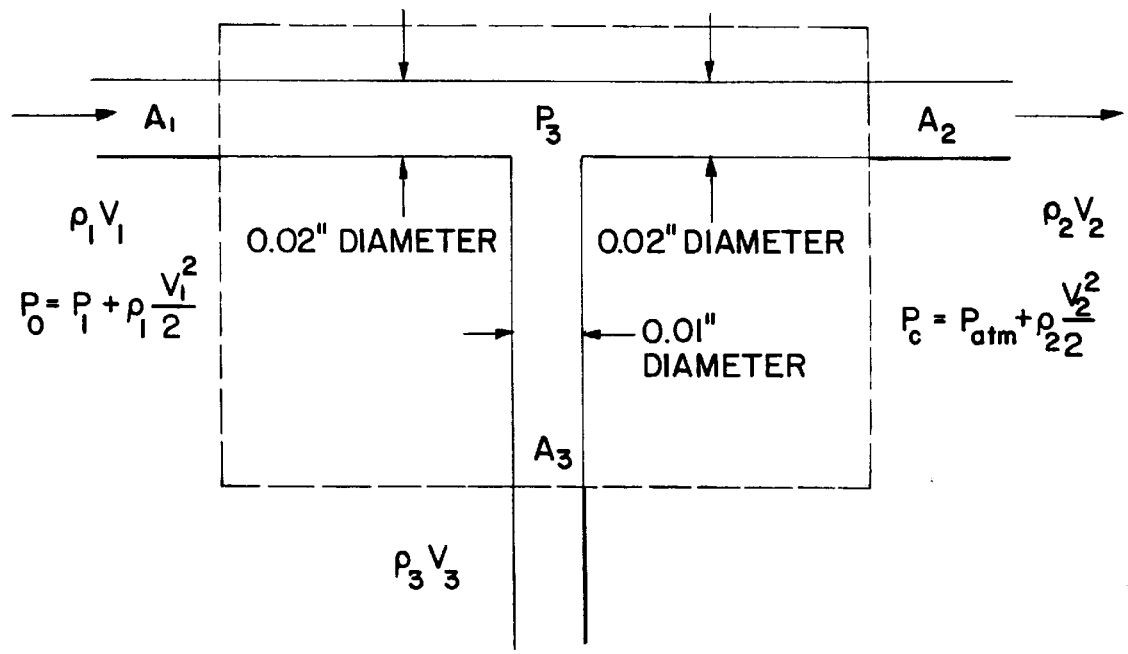
FIG. 8 is a schematic, side view of a venturi form of pump.
Figure 10A:
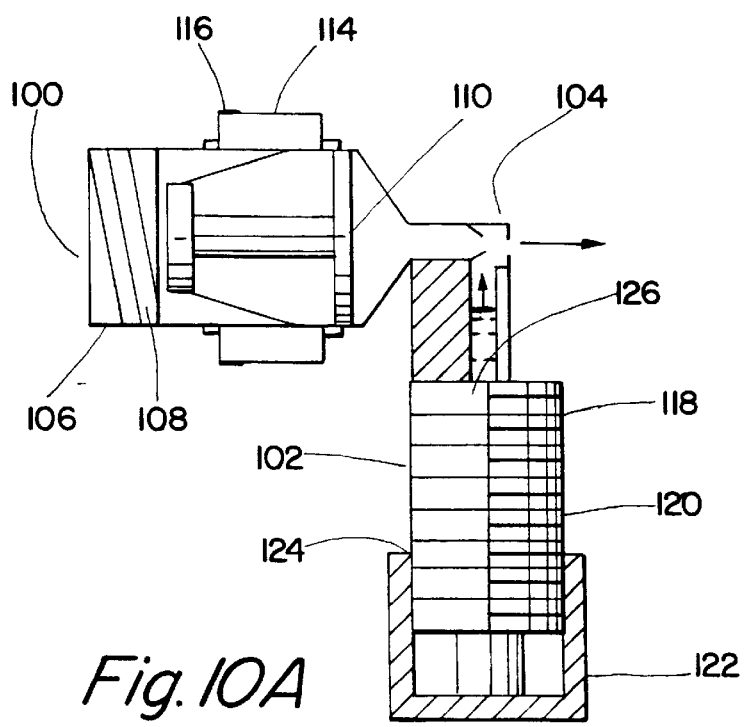
FIG. 10 is a schematic, cutaway front view of another embodiment of the invention employing a jet pump mechanism for inducing and metering a liquid into an air stream.
Figure 10B:
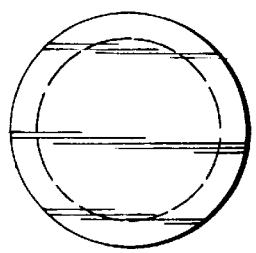
Figure 9A:
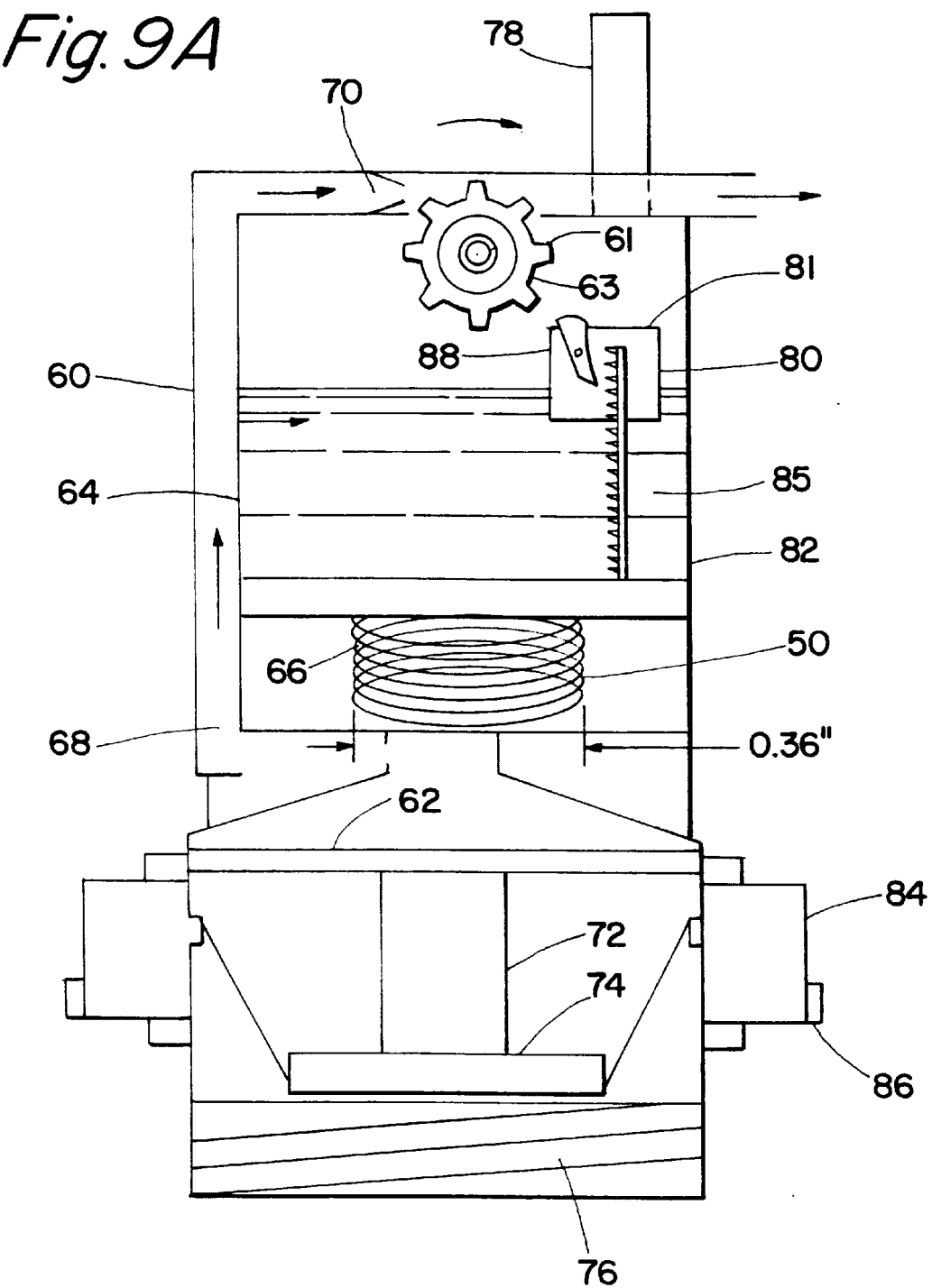
FIG. 9A is a schematic, cutaway, longitudinal view of an embodiment of the invention employing a metering wheel or paddle wheel to feed a liquid for induction into a gas stream.
Figure 9B:
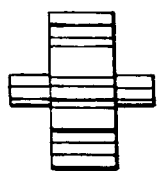
FIG. 9B is a front view of the metering wheel in FIG. 9A.
Figure 11:
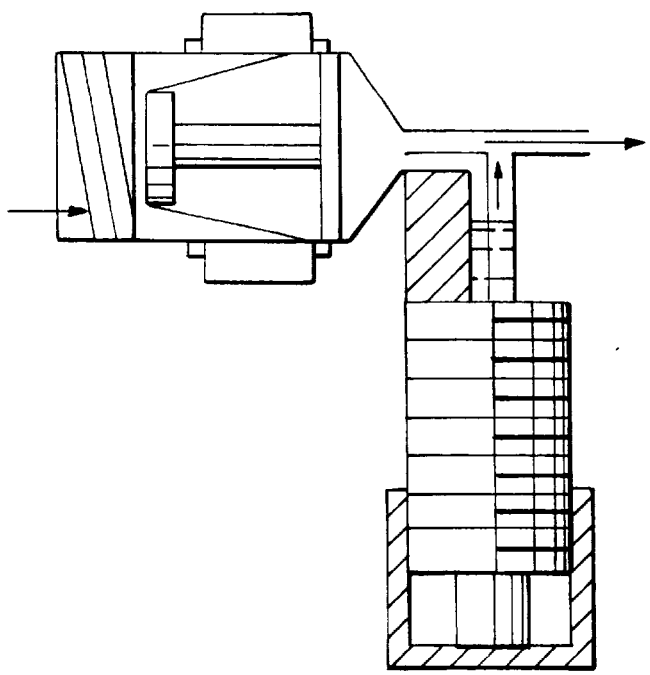
FIG. 11 is a schematic view of the device of FIG. 10 showing a venturi in place of the jet pump of FIG. 10.
Figure 12A:
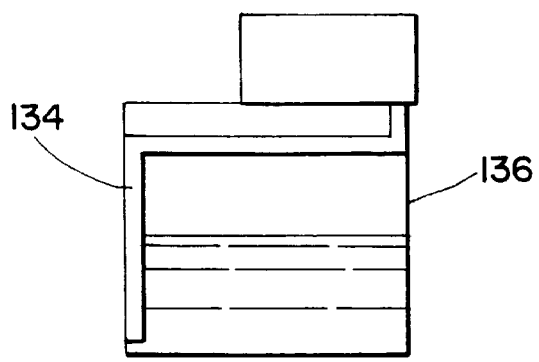
FIG. 12 is a schematic view of another embodiment of the invention enabling use of the device in a horizontal or vertical position.
Figure 12B:
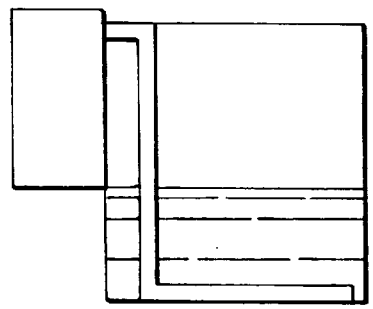

Continuity of mass flow for steady state demands that the flow of mass into the tube equals the flow of mass out of the tube. It can be demonstrated that behavior of the venturi, and the use of stagnation pressure, induces the separation, metering, and delivery of the fluid solution similarly to the jet pump. FIG. 8 shows how to analyze the venturi and feeder tube portion of this system using a control volume. The analysis proceeds by enforcing conservation of mass and momentum flow in and out of a well defined volume in space, specifically the venturi and feeder tubes. The continuity of mass flow is:

$$\rho_1 A_1 V_1 = \rho_2 A_2 V_2 + \rho_3 A_3 V_3 \tag{14}$$

where $A_1$, $A_2$, and $A_3$ are the cross sectional areas of the three passages, and $\rho 1$, $\rho 2$, and $\rho 3$ are the average densities of the fluids flowing through the passages. If the volume of the mass flowing in area $A_3$ is small compared to the volume of the fluid across areas $A_1$ and $A_2$, then the volume change of the gas is negligible. From the data given previously, this is the case. Furthermore, if the areas $A_1$ and $A_2$ are the same, then $V_1$ must equal $V_2$. This is not a requirement for operation, but it is convenient for manufacturing.

If only a very small amount of solution is metered into the passage, then the difference in pressure on the fluid in the feeder tube may be expressed as:

$$P_0 - P_3 = \frac{V_1^2}{2}\rho_1 \tag{15}$$

where $V_1$ is the velocity of the gas in the venturi and $P_3$ the static pressure at port 3 in FIG. 8. To calculate the velocity, the mass of the suction fluid after it has mixed with the motive gas must be included. Thus, Bernoulli's equation, which represents conservation of momentum flow for this system is:

$$P_0 = P_{atm} + \rho_2 \frac{V_1^2}{2} \tag{16}$$

where $\rho_2$ is the same as equation (8), and is the average mass density of the mixture. $P_{atm}$ is the atmospheric pressure into which the mixture is ejected. Thus, the determining factor is again the mixing ratio, r, which will give the ratio of the volumes of the ejected fluid to the motive gas. Note that the suction into the venturi is calculated from the mass density of the motive gas alone, while the velocity of the mixture is calculated from equation (16).

Equations 15 and 16 may be combined and solved for the mixing ratio, r, in a manner similar to that used to derive equation 12. The expression for the mixing ratio, r, is:

$$r = \frac{P_s - \Delta P}{\Delta P - P_s\left(\frac{\rho_s}{\rho_1}\right)} \tag{17}$$

$$\Delta P = P_0 + P_{atm} \tag{17a}$$

$$P_s = P_0 - P_3 \tag{17b}$$

This equation gives the mixing ratio directly in terms of the motive pressure, the ambient pressure, and the suction pressure, $P_0$, $P_{atm}$, and $P_s$, respectively.

It should also be noted that the approximation of incompressible flow made here is not exact. If, as is shown in FIG. 7, the venturi tube is the same diameter before and after the suction fluid tap, then motive gas must compress slightly to allow for the presence of the suction fluid.

However, the suction fluid is typically of high density and small volume compared to the motive gas. This means that neglecting the compression (from the previous data, 1 part in $10^3$) will not result in significant error.

The motive pressure difference is equal to the square of the velocity multiplied by one half of the density of the motive gas. This pressure difference only exists if the motive gas is in motion. The discharge of the fluid into the air passage way has the effect of reducing the flow velocity, and hence the difference in pressure. The process is self-regulating, and the flow may be determined. If a piston is supplying 5 kPa of pressure and the motive gas is air, a mixing ratio of about 30 $\mu$l/ml is calculated for this method. Losses due to turbulence and mixing reduce this number similarly to the jet pump.

The solution is ejected as a series of small droplets from the end of the nozzle, and hence onto the eye. The controlled volume of gas from the driving piston, and the known pressure applied to the piston determine the amount of fluid to be delivered. The limiting forces determining the delivery are the pressure in the container, the viscosity, gravity, and surface tension forces in the feeder tube, and reduced static pressure in the venturi due to the increase in the flow velocity. It may also be desirable for very high viscosity solutions to restrict the flow of gas into the solution reservoir; this will reduce the rate of pressure rise in the reservoir, and reduce the relative flow of fluid into the chamber.

An embodiment of the invention which employs a metering wheel is shown in FIG. 9. The metering wheel 63 serves to separate and meter the flow of a fluid solution into an air passage for induction ejection to the eye. This embodiment performs a method which is basically related to the methods of the previous embodiments. It is envisioned that this embodiment will be preferable for delivery of fluids with higher viscosity.

The metering wheel embodiment includes a housing 60, piston 62, reservoir 64, bellows 66, air passageway 68, nozzle 70, shaft 72, centralizer 74, spring 76, extension tube 78 and level controller 80 and piston 82. This embodiment also includes a cocking mechanism and release mechanism similar to that shown in FIG. 1. The cocking mechanism includes a twist sleeve or ring 84 and one or more catches spring loaded by spring struts 86. The sleeve 84 has an inclined groove or track in its interior surface for each catch and along with the catches moves when being cocked.

The release mechanism includes a manually operated sliding button or post 86 which releases the catches, thereby enabling the spring 76 to drive the piston 62 upward. The piston, in turn, displaces gas against the bellows 66 and flows through passageway 60 and nozzle 70. The bellows 66 acts against the piston 82 which cooperates with the level controller 80 to maintain a desired level of fluid in the reservoir. The fluid level is such as to immerse teeth or paddles 61 when at the bottom of the wheel 63.

Gas exiting the nozzle 70 turns the wheel 63 and induces a fluid solution on the exterior surface of the wheel to mix with the gas stream. The mixture then ejects from the gas passageway to impinge on an eye or other desired body part.

The level controller 80 in FIG. 9 includes a floating ring 84, a bar ratchet 86, and a locking pawl or tooth 88. The lower end of the ratchet 86 contacts the piston 82 and is free to move within the ring 84 and the extension tube 78. The pawl or tooth 88 is pivotally mounted on the ring 86 and has a cam surface on one end and a tooth on the other. It is dimensioned such that when the cam surface contacts the top end of the reservoir 64, the tooth end engages and locks movement of the ratchet 86. The locking action is selected to occur in a preferred embodiment when the fluid level immerses the teeth 61 of the wheel 63. The locking action also fixes the position of the piston 82 until the level of fluid diminishes. It will be appreciated that the pawl 88 may alternately be pivotally attached to the top of the reservoir 64 and still be actuated by a float such as the ring 84 to lock the ratchet 86. As is apparent, the diameter of float 84 should be greater than the diameter of the extension tube 78.

Extension tube 78 allows the ratchet 86 to extend up past the top of the reservoir 64 to prevent spillage of the solution. The ratchet extends further up into the tube as the solution is used. The inner diameter is large enough to allow the ratchet 86 to freely slide in and out without impediment.

The ratchet extension 86 effectively connects the sliding piston 82 with the float 84 and engages the locking tooth 88 to prevent the piston 82 from moving any further upward when the fluid in the reservoir reaches an intended or predetermined level. The ratchet extension is approximately ½" to ¾" long, and is cylindrical in shape with one side consisting of serrated teeth. This side is also flattened slightly to help prevent the float from rotating with respect to the extension.

The spring strut 86 is attached to the lower part of the piston 62—i.e., the disk 74—and also has a catch or engaging member for the twist ring 84. This catch is pressed backward when the release button 86 is pushed, and enables the air piston 62 to move upward.

FIG. 10 is a schematic layout of an embodiment of the invention which involves a two-step gas induction procedure using a pump to eject fluid. The apparatus in this embodiment includes three principal components—a source of metered compressed gas or air 100, a source of a metered fluid solution 102, and a pump 104, in this case, a jet pump. The source of metered gas or air 100 is very similar in principle and components to the gas or air source of FIG. 9A, and its major components are only mentioned here. They include a housing 106, a spring 108, a piston 110, an gas or air passageway 112, a twist sleeve 114 and a cocking and releasing assembly 116.

The source of metered fluid 102 includes a fluid reservoir 118 with an external thread 120, an internally threaded cap 122 and piston 124 assembly, and a metering tube 126. Threading of the cap 122 onto the housing forces the piston 124 upward in the fluid solution reservoir 118 and the tube 126. The tube 126 is preferably calibrated and clear so that a known amount of a fluid solution is ready for ejection. Actuating the spring 108 forces a known or metered amount of air through the passage 112 and the jet pump 104, thereby inducing a fixed quantity of the fluid solution to be ejected.

The volume to be delivered is determined precisely by the dimensions of the chamber. In FIG. 10 this is accomplished by turning the thumbwheel 122 to force a predetermined amount of solution into the clear chamber 126 of desired volume where it can be observed. When it is observed to be fill, the piston 110 is cocked by the twist ring 114 similar to the previous embodiments. The device is pointed towards the eye, and it is activated when the spring 108 is released by the release assembly on the twist ring. The air from the piston 110 is predetermined to be sufficient to remove the fluid from the clear tube 126 and eject it to the eye. Because the metering is accomplished by precisely displacing the piston 124 in the solution reservoir, very accurate determination of delivery of small volumes becomes possible.

The clear tube 126 dimensions are typically such that when the tube is full a selected volume (e g. 10 μl) of solution will be delivered. When chamber is half full, only 5 μl of solution will be delivered. The user can see the solution in the tube and judge when it is full without having to possibly waste any solution. The advantage of this method over the single step method is that the device is not required to be held in an upright position to operate. A further advantage of this method over the single step method is that the metering can be very precise with additional safety provided from accidental overdose.

EXAMPLE 2

This example illustrates the use of the novel delivery system described in Example 1.

An initial evaluation was undertaken using five normal volunteers with symmetrical intraocular pressures having no ocular or systemic disease and taking no medications. On the study day each volunteer at Hour 0 (HrO) had his/her intraocular pressure (IOP) measured by applanation tonometry. Blood pressure (BP) and pulse rate(P) were measured at the same time. Results obtained from this preliminary study on five human volunteers have overlapping times (see Table 3 below) since subjects did the study on different days. After at least 30 min and no more than 1 h, each volunteer received 5 μl of 0.25 % timolol hemihydrate (Betimol) to the right eye (OD) and nothing to the left eye (OS). Timolol is a β-blocker with ocular effects of decreasing the intraocular pressure and potential systemic side effects of bronchoconstriction, decreasing blood pressure and decreasing heart rate. The device of the invention used to deliver the dose was a prototype that was calibrated so that the volume of solution given was known from the volume of air displaced. The device was a one-step gas induction delivery device that used a jet pump to deliver the medicine. The person giving the dose was not involved in the evaluation of the volunteer. Two h later intraocular pressure, blood pressure and pulse rate was again measured. The blood pressure included both systolic and diastolic readings.

This preliminary study demonstrates the safety and feasibility in normal human volunteers of one step gas induction delivery. The nonselective β antagonist timolol was chosen as the agent of delivery because of its common use in clinical practice, its known potential systemic and local side effects, and its known ability to lower intraocular pressure in normal human subjects. No elicited or volunteered subjective complaints accompanied the drug delivery to the right eye. No consistent effect was observed on pulse rate or systemic blood pressure. Only one subject did not respond with a reduction of intraocular pressure in the treated right eye. The reduction in intraocular pressure in these normal volunteers is consistent with that in the ophthalmic literature using standard bottle delivery (1). The standard clinical delivery of timolol is 30 μl of a 0.5% solution. This yields a dose of 150 μg to the eye. In this study a dose of only 12.5 μg was delivered to the eye. This is a twelve fold reduction in dose with no apparent loss of pressure lowering effect.

Discussion for this apparatus has focused on the use of the delivery of small controlled volumes of ophthalmic liquids. Other uses for this invention include, but are not limited to, solution delivery involving the following body organs and fields of medicine:

Ear (Otic)
Nose (Nasal) and Throat
Dental/Oral
Dermatologic
Wound Healing
Cardiovascular
Oncology/Chemotherapy
Endocrine
Central Nervous System
Urologic/Genital
Gynecologic/Obstetrical
Rectal
General Surgical

TABLE 3

Effects of using 0.25% Betimol dosing OD

| | Hour Zero Data | | | Dose Time | Second Hour Date | | |
|---|---|---|---|---|---|---|---|
| Patient | Time | IOP | BP/P | Time | Time | IOP | BP/P |
| CD | 9:35 AM | 12/12 | 112/84–74 | 10:32 AM | 12:25 PM | 9/11 | 112/78–86 |
| KN | 9:38 AM | 14/14 | 98/65–69 | 10:30 AM | 12:27 PM | 9/12 | 100/61–68 |
| CA | 9:45 AM | 16/16 | 95/75–66 | 10:32 AM | 12:29 PM | 16/16 | 108/72–88 |
| KZ | 9:47 AM | 18/18 | 116/72–66 | 10:31 AM | 12:31 PM | 13/16 | 117/70–72 |
| RR | 8:35 AM | 20/20 | 154/97–74 | 8:35 AM | 10:25 AM | 14/18 | 148/88–53 |

No volunteer offered any subjective complaints at the time of dose delivery to the right eye. No redness or other ocular signs were observed after dosing. No reflex tearing, blinking, or wiping was observed. Each subject except for one (CA) had a decrease in intraocular pressure in the right eye. The percent reduction at Hour 2 using the left eye's intraocular pressure at Hour 2 as the control ranged from 13% to 25%. Two subjects had a decrease in pulse rate at Hour 2. One of these subjects had a pulse rate change from 69 at baseline to 68 at Hour 2. The other three subjects demonstrated a substantial increase in pulse rate ranging from 6 to 12 beats per min. Only one subject had a decrease in blood pressure. All other subjects had essentially no change in blood pressure.

Gastrointestinal
Pulmonary
Orthopedic
Pediatric

All of the methods and apparatus disclosed and claimed herein may be made and executed without undue experimentation in light of the present disclosure. While the methods and apparatus of this invention have been described in terms of preferred embodiments, it will be apparent to those of skill in the art that variations may be applied to the methods and apparatus and in the steps or in the sequence of steps of the method described herein without departing from the concept, spirit and scope of the invention. All similar substitutes and modifications apparent to those skilled in the art are deemed to be within the spirit, scope and concept of the invention as defined by the appended claims.

REFERENCES

The following references, to the extent that they provide exemplary procedural or other details supplementary to those set forth herein, are specifically incorporated herein by reference.

Bartlett and Jaanus, In Clinical Ocular Pharmacology, 2nd Edition, Butterworths, London, 5:95–148, 1989.

Brown, Hotchkiss, Davis, "Creating Smaller Eyedrops by Reducing Eyedropper Tip Dimensions," American Journal of Ophthalmology, 99:460–464, 1985.

Brown, Lynch, Wood, Osetinsky, Schoenwald, "Reducing Eyedrop Size Decreases Systemic Absorption of 10% Phenylephrine," Invest. Ophthalmic. and. Vis. Sci., 27(Suppl):102, 1986.

Brown, Wood, Lynch, Schoenwald, Chien, Jennings, "Improving the Therapeutic Index of Topical Phenylephrine by Reducing Drop Volume," Ophthalmology, 94:847–850, 1987.

Chrai, Makoid, Eriksen, Robinson, "Drop Size and Initial Dosing Frequency Problems of Topically Applied Ophthalmic Drugs," J. Pharm. Sci., 63:333–338, 1974.

Chrai, Patton, Mehta, Robinson, "Lacrimal and Instilled Fluid Dynamics in Rabbit Eyes," J Pharm. Sci., 62:1112–1121, 1973.

Edman, P., Editor, In: Pharmacokinetics of Ocular Drug Delivery, CRC Press, Boca Raton, Florida, 159–191, 1993.

File and Patton, "Topically Applied Pilocarpine," Arch. Ophthalmic., 98:112–115, 1980.

Fox and McDonald, In: Introduction to Fluid Mechanics Fourth Edition, Wiley and Sons, New York, 4:96–192, 1992.

Gosline and O'Brien, In: The Water Jet Pump, California University Publications, 1937.

Gray, "The Influence of Drop Size on Pupil Dilatation," Eye, 5:615–619,1991

Himmelstein, Guvenir, Patton, "Preliminary Pharmacokinetic Model of Pilocarpine Uptake and Distribution in the Eye," J Pharm. Sci., 67:603–606, 1978.

Jumpeter, "Jet Pumps," In: Pump Handbook, Second Edition 4:1–27, 1986.

Lynch, Brown, Goode, Schoenwald, Chien, "Reduction of Phenylephrine Drop Size in Infants Achieves Equal Dilation With Decreased Systemic Absorption," Arch. Ophthalmic., 105:1364–1365, 1987.

Patton and Francoeur, "Ocular Bioavailability and Systemic Loss of Topically Applied Ophthalmic Drugs," Amer. J. Ophthalmic., 85:225–229, 1978.

Patton, 1977 "Pharmacokinetic Evidence for Improved Ophthalmic Drug Delivery by Reduction of Instilled Volume," J. Pharm. Sci., 66:1058–1059, 1977.

Petursson, Cole, Hanna, "Treatment of Glaucoma using Minidrops of Clonidine," Arch. Ophthalmic., 102:1180–1181, 1984.

Sears, M. L., Editor, "Pharmacology of the Eye," Springer-Verlag, Berlin, 1984,

Shell, 1982, "Pharmacokinetics of Topically Applied Ophthalmic Drugs," Survey of Ophthalmology, Jan–Feb., 26:207–218, 1982.

U.S. Pat. No. 3,934,585

What is claimed is:

1. An unitary apparatus for delivering a liquid as droplets which comprises:

a cylindrical housing having a closed top;

a compartment in an upper portion of the housing adapted to contain the liquid;

a piston and cylinder assembly positioned within the housing proximate the compartment;

a spring positioned within the housing;

a cocking device operable to hold the piston within the cylinder against the spring to a cocked position;

an eductor pump positioned proximate the housing and including an inlet and an outlet for the flow of gas through the pump and a port to enable said liquid to enter the pump from the compartment for mixing with the gas flow;

a passageway interconnecting the cylinder with said inlet connection to enable gas to flow from the cylinder to said inlet in response to movement of the piston from said cocked position;

a release mechanism operable to release the piston from said cocked position and thereby enable the piston to force a quantity of gas to flow through said passageway and said pump;

a feeder interconnecting the port of the pump with the liquid in said compartment to thereby educt a quantity of said liquid in response to the flow of said gas through the pump;

the piston displacement and the sizes of the pump and the feeder being interrelated such that said quantity of gas educts and delivers a predetermined volume of said liquid to as droplets through said outlet.

2. An apparatus as defined in claim 1, wherein the pump comprises a jet pump.

3. An apparatus as defined in claim 1, wherein the pump comprises a venturi.

4. An apparatus as defined in claim 1, wherein the pump comprises a paddle wheel.

5. An apparatus for instilling a liquid in the eye or other body part which comprises:

a cylindrical housing having a closed top;

a compartment in an upper portion of the housing adapted to contain multiple doses of the liquid;

a piston positioned within the housing below the compartment and movable along the housing in a piston and cylinder relation;

a spring positioned within the housing between the piston and the bottom of the housing;

a cocking device operable to force the piston downward within the cylinder and against the spring to a cocked position;

an eductor pump positioned proximate the top of the housing and including inlet and outlet connections for the flow of gas through the pump and a port to enable said liquid to enter the pump for mixing with the gas flow;

a passageway interconnecting the cylindrical housing above the piston with said inlet connection to enable gas to flow from the housing to said inlet in response to upward movement of the piston from its cocked position;

a release mechanism operable to release the piston from its cocked position and thereby enable the piston to force a quantity of gas to flow through the passageway and the eductor pump;

a feeder conduit interconnecting the port of the eductor pump with the liquid in said compartment to thereby educt a quantity of said liquid in response to the flow of said gas through said eductor pump;

the piston displacement and the sizes of the eductor pump and the feeder conduit being interrelated such that said quantity of gas educts and delivers a single dose less than 30 ml of said liquid to the eye as droplets.

6. An apparatus for instilling a liquid in the eye which comprises:

a cylindrical housing having a closed top;

a compartment in an upper portion of the housing adapted to contain multiple doses of the liquid;

a piston positioned within the housing below the compartment and movable along the housing;

a spring positioned within the housing between the piston and the bottom of the housing;

a cocking device operable to force the piston downward within the cylinder and against the spring to a cocked position;

a jet pump positioned proximate the top of the housing and including inlet and outlet connections for the flow of gas through the pump and a port to enable liquid to enter the pump for mixing with the gas flow;

a passageway interconnecting the cylindrical housing above the piston with said inlet connection to enable gas to flow from the housing to said inlet in response to upward movement of the piston from its cocked position;

a trigger operable to release the piston from its cocked position and thereby enable the piston to force a quantity of gas to flow through the passageway and the jet pump;

a feeder conduit interconnecting the port of the jet pump with the liquid in said compartment to thereby educt a quantity of said liquid in response to the flow of said gas through the jet pump;

the piston displacement and the sizes of the jet pump and the feeder conduit being interrelated such that said quantity of gas educts and delivers a single dose of said liquid to the eye as droplets with an aggregate volume less than the capacity of the eye to hold.

7. A unitary device as defined in claim 6, wherein the dose of said liquid is between about 1 ml and about 15 ml.

8. A method as defined in claim 6 wherein the dose of said liquid is between about 1 ml and about 25 ml.

9. A method for delivering a unit dose of a liquid as droplets to the eye or other body part which comprises:

(a) providing having a driving inlet, a suction inlet, and an outlet, and being capable of educting and ejecting a preselected unit dose of a liquid from a reservoir of the liquid upon the flow of a preselected volume of a particular gas at a particular pressure through the pump;

(b) delivering said preselected volume of said particular gas at said particular pressure to the driving inlet of the pump to thereby educt a unit dose of the liquid from the reservoir into the gas flowing through the pump and form a mixture of the gas and droplets of the liquid dose; and (c) ejecting the mixture of gas and liquid dose droplets toward the eye or other body part.

10. A device for delivering a liquid aqueous ophthalmic preparation to an eye, comprising a unitary structure including:

a housing having a closed top;

a compartment in the housing adapted to contain the preparation;

a pump within the housing including inlet and outlet connections for the flow of air through the pump and a port to enable liquid to be drawn into the pump for mixing with the air flow;

a spring loadable piston having a one-way valve positioned within the housing and moveable within the housing;

a cocking device manually operable to force the piston within the housing to a cocked spring loaded position;

a passageway interconnecting the housing with said inlet connection to enable air to flow from the housing to said inlet in response to movement of the piston from its cocked position;

a mechanism operable to release the piston from its cocked position and thereby enable the piston to force a volume of air to flow through the passageway and the pump; and a feeder conduit interconnecting the port of the pump with the aqueous preparation in said compartment to thereby educt a quantity of said preparation in response to the flow of said air through said pump;

the piston displacement and the sizes of the pump and feeder conduit being interrelated such that said volume of air educts and delivers a predetermined volume less than 30 $\mu$l of said liquid as droplets.

* * * * *